United States Patent
Leng

(10) Patent No.: US 12,357,784 B2
(45) Date of Patent: Jul. 15, 2025

(54) POSITIONING AND STABILISING STRUCTURE FOR A PATIENT INTERFACE

(71) Applicant: RESMED ASIA PTE. LTD., Singapore (SG)

(72) Inventor: Wai Hoong Leng, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 1001 days.

(21) Appl. No.: 17/431,543

(22) PCT Filed: Feb. 14, 2020

(86) PCT No.: PCT/IB2020/051268
§ 371 (c)(1),
(2) Date: Aug. 17, 2021

(87) PCT Pub. No.: WO2020/170100
PCT Pub. Date: Aug. 27, 2020

(65) Prior Publication Data
US 2022/0134042 A1    May 5, 2022

(30) Foreign Application Priority Data
Feb. 18, 2019  (AU) .............................. 2019900507

(51) Int. Cl.
*A61M 16/06*    (2006.01)

(52) U.S. Cl.
CPC .... *A61M 16/0683* (2013.01); *A61M 16/0616* (2014.02); *A61M 16/0622* (2014.02);
(Continued)

(58) Field of Classification Search
CPC .......... A61M 16/0683; A61M 16/0605; A61M 16/0633; A61M 16/0616; A61M 16/0622
See application file for complete search history.

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| CN | 102245250 A | 11/2011 |
| CN | 105120935 A | 12/2015 |

(Continued)

OTHER PUBLICATIONS

Japanese Notice of Allowance for Application No. JP2021-571058, three pages, dated Jan. 9, 2024.
(Continued)

*Primary Examiner* — Joseph D. Boecker
*Assistant Examiner* — Brian T Khong
(74) *Attorney, Agent, or Firm* — Nixon & Vanderhye P.C.

(57) ABSTRACT

A patient interface includes a positioning and stabilising structure having headgear comprising a ring strap portion with a superior portion configured to overlay the parietal bones of the patient's head in use and an inferior portion configured to overlay or lie inferior to the occipital bone of the patient's head in use. The ring strap portion defines a loop having a pair of upper strap portions configured to connect between the ring strap portion and a cushion assembly in use on a respective side of the patient's head superior to an otobasion superior. The headgear may comprise a rigidised portion. The headgear may be integrally formed by flat knitting and the strap portions may include blind guides to provide tactile indications of the locations of fastening portions.

36 Claims, 33 Drawing Sheets

(52) U.S. Cl.
CPC ................ *A61M 2205/582* (2013.01); *A61M 2210/0618* (2013.01)

(56) References Cited

U.S. PATENT DOCUMENTS

| | | | |
|---|---|---|---|
| 5,687,715 | A | 11/1997 | Landis |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2013/0199537 | A1* | 8/2013 | Formica ............ A61M 16/0816 128/205.25 |
| 2014/0209098 | A1* | 7/2014 | Dunn ................... D04B 1/22 112/475.11 |
| 2015/0128953 | A1* | 5/2015 | Formica ............. B32B 15/046 128/206.21 |
| 2015/0217074 | A1* | 8/2015 | Wells ............... A61M 16/0683 128/207.18 |
| 2016/0006744 | A1 | 1/2016 | Du et al. |
| 2016/0067441 | A1 | 3/2016 | Bearne et al. |
| 2016/0256655 | A1 | 9/2016 | Mah et al. |
| 2017/0182276 | A1 | 6/2017 | Hammer et al. |
| 2017/0326320 | A1 | 11/2017 | Baigent et al. |
| 2018/0126108 | A1 | 5/2018 | Formica et al. |
| 2018/0140795 | A1 | 5/2018 | Wells et al. |
| 2018/0221191 | A1 | 8/2018 | Scott et al. |
| 2018/0333292 | A1 | 11/2018 | Blaszczykiewicz et al. |
| 2019/0099575 | A1 | 4/2019 | Edwards et al. |
| 2020/0009345 | A1 | 1/2020 | Wells et al. |

FOREIGN PATENT DOCUMENTS

| | | |
|---|---|---|
| CN | 106912194 A | 6/2017 |
| CN | 107920608 A | 4/2018 |
| JP | 1998-314307 | 12/1998 |
| JP | 2014-529432 A | 11/2014 |
| JP | 2015-119995 | 7/2015 |
| JP | 2015-522381 A | 8/2015 |
| JP | 2017-535370 | 11/2017 |
| JP | 2019-501734 | 1/2019 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2013/026091 A1 | 2/2013 |
| WO | 2014/015382 A1 | 1/2014 |
| WO | WO 2014/110622 A1 | 7/2014 |
| WO | WO 2015/006826 A1 | 1/2015 |
| WO | 2016/043603 A1 | 3/2016 |
| WO | WO 2016/082001 A1 | 6/2016 |
| WO | WO 2017/015701 A1 | 2/2017 |
| WO | WO 2017/049361 A1 | 3/2017 |

OTHER PUBLICATIONS

International Preliminary Report on Patentability mailed Jan. 20, 2022 in related PCT Application PCT/SG2020/050465.
Extended European Search Report mailed Apr. 7, 2022 in corresponding EP Application 20759364.1.
Extended European Search Report for related EP Application No. 20918464.7, nine pages, dated Jul. 31, 2023.
Examination Report No. 1 in corresponding Australian Application No. 2020224386, three pages, dated Sep. 4, 2024.
Extended European Search Report in corresponding Application No. EP 24150946.2, 11 pages, dated Jul. 7, 2024.
"*Respiratory Physiology*", by John B. West, Lippincott Williams & Wilkins, 9th edition published 2012 (8 pages).
International Search Report mailed May 12, 2020 in corresponding PCT Application PCT/IB2020/051268 (21 pages).
Written Opinion mailed May 12, 2020 in corresponding PCT Application PCT/IB2020/051268 (10 pages).
Second Written Opinion mailed Jan. 15, 2021 in corresponding PCT Application PCT/IB2020/051268 (9 pages).
International Preliminary Report on Patentability mailed May 28, 2021 in corresponding PCT Application PCT/IB2020/051268 (50 pages).
First Office Action with English Translation in corresponding CN Application No. 202080027626.5, 21 pages, dated Nov. 7, 2025.
First Office Action with English Translation in related CN Application No. 202080095772.1, 15 pages, dated for Jan. 3, 2025.
Notice of Reasons for Refusal with English Translation in corresponding JP Application No. 2024-017452, seven pages, dated Nov. 25, 2024.

* cited by examiner

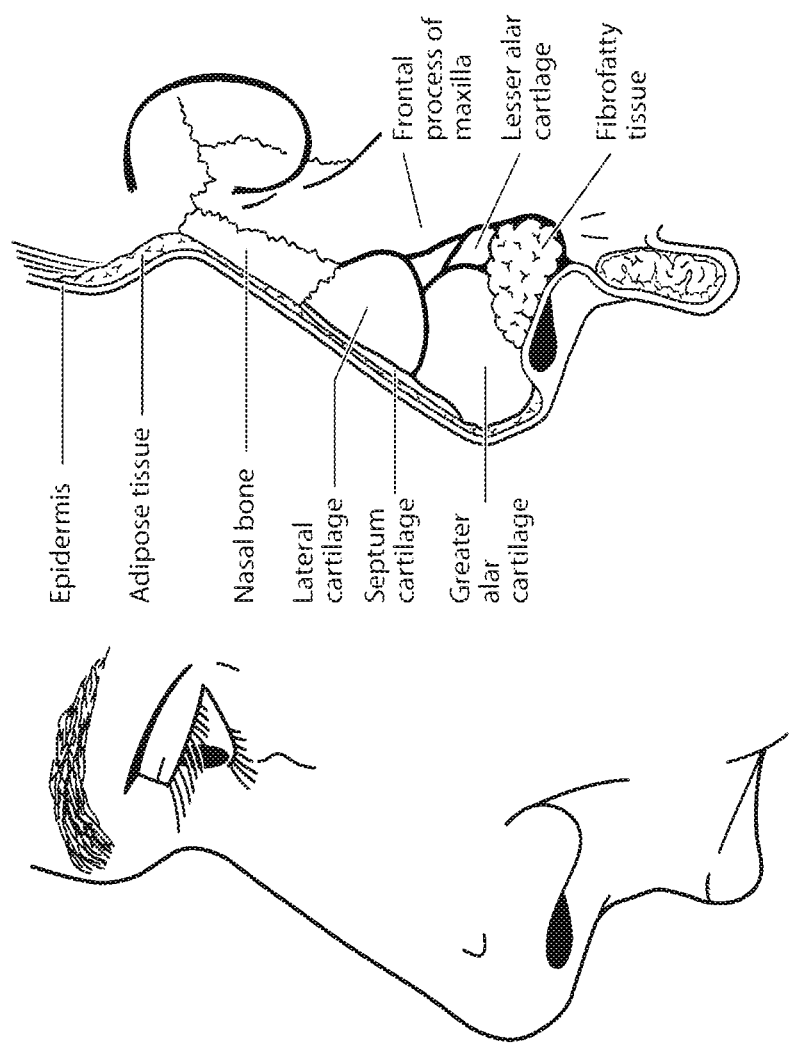
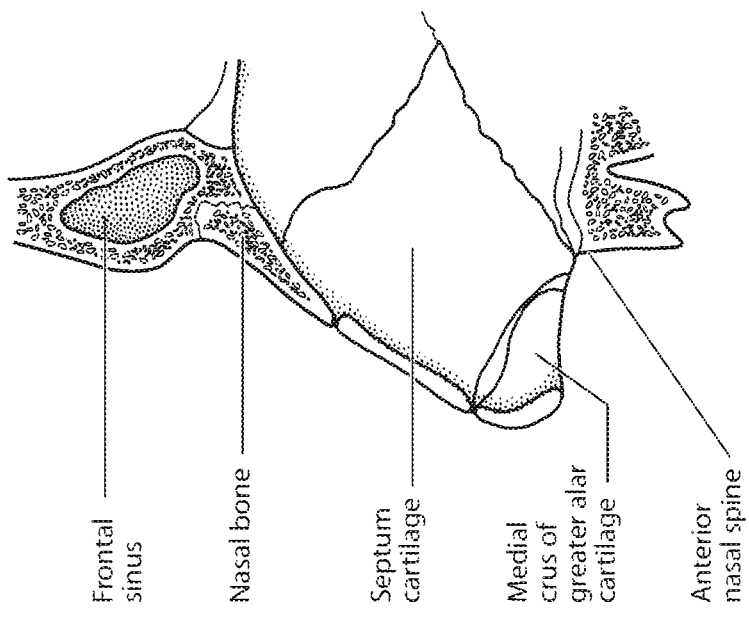
FIG. 2G
FIG. 2H
FIG. 2I

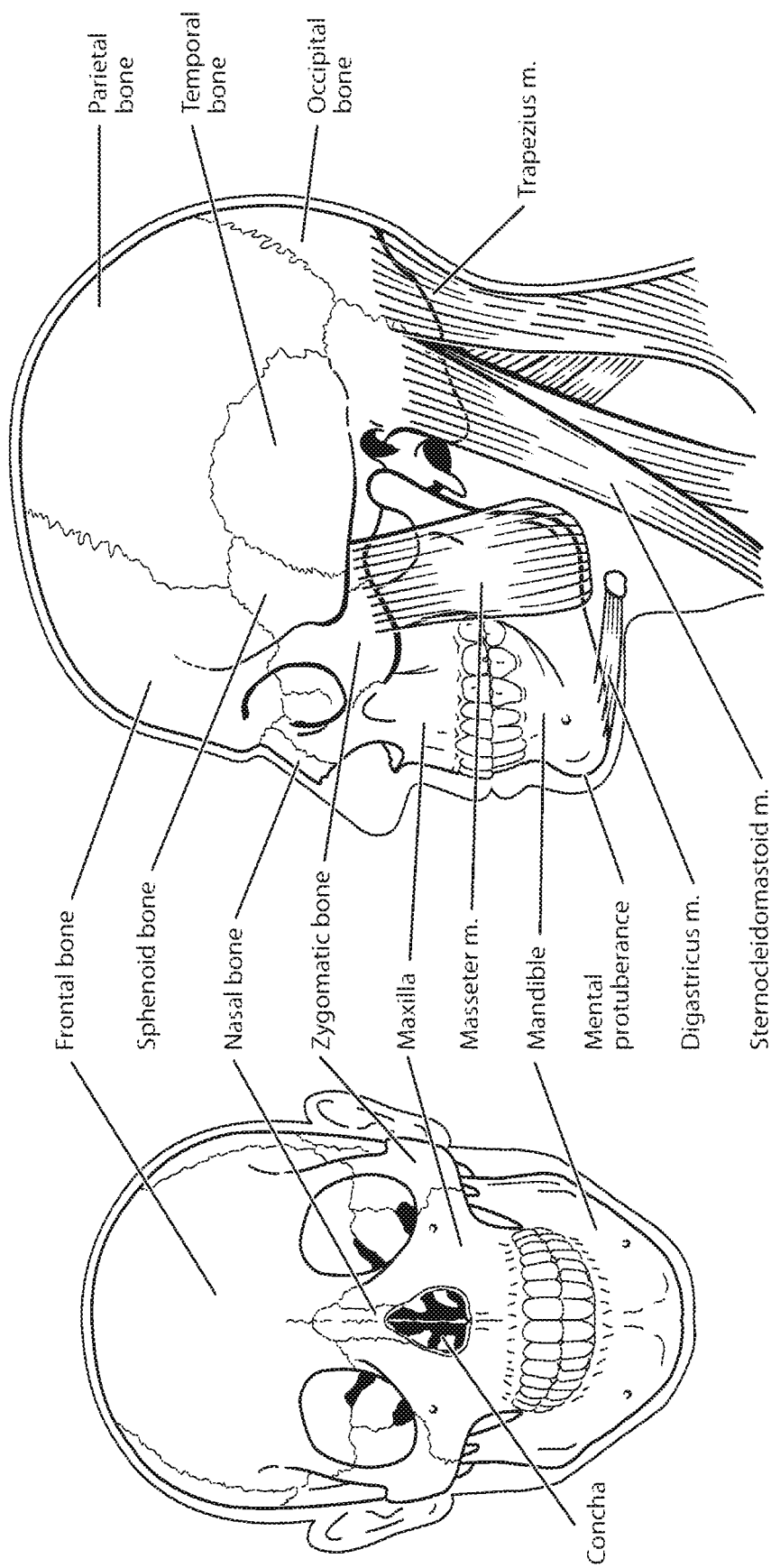

Relatively Large Positive Curvature

Relatively Small Positive Curvature

Zero Curvature

Relatively Small Negative Curvature

Relatively Large Negative Curvature

Left-hand rule
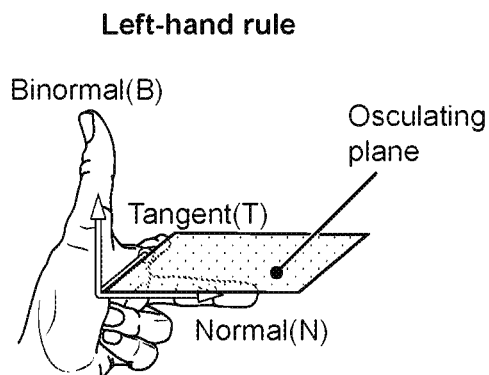
FIG. 3O
Right-hand rule
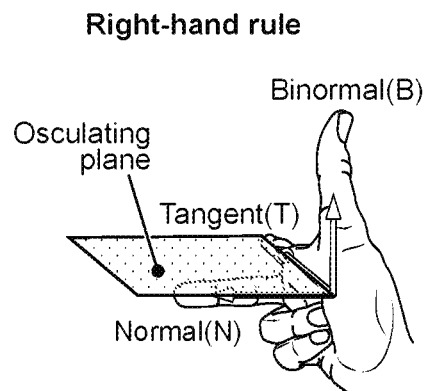
FIG. 3P
Left ear helix
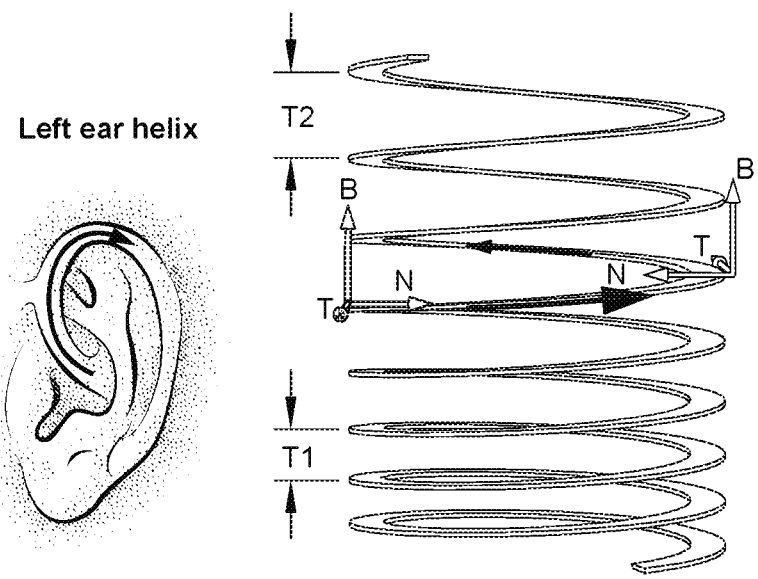
Right ear helix
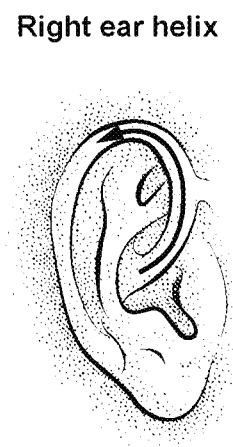
FIG. 3Q
Right-hand helix
Right-hand positive
FIG. 3S
FIG. 3R
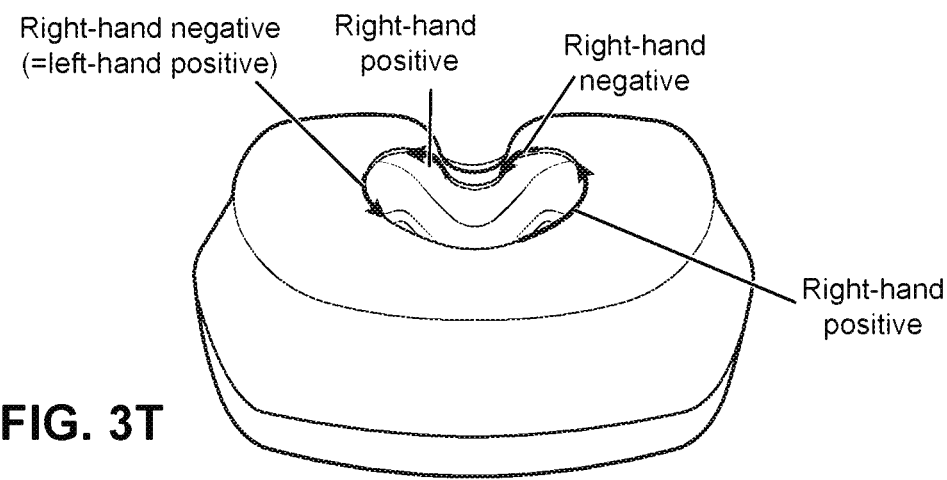
FIG. 3T

POSITIONING AND STABILISING STRUCTURE FOR A PATIENT INTERFACE

1 CROSS-REFERENCE TO RELATED APPLICATIONS

This application is the U.S. national phase of International Application No. PCT/IB2020/051268 filed Feb. 14, 2020 which designated the U.S. and claims priority to Australian Provisional Application No. 2019900507 filed Feb. 18, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a positioning and stabilising structure for a patient interface, the positioning and stabilising structure comprising an integrally formed strap that is formed by flat knitting. The strap may connect to a frame or plenum chamber of the patient interface via four connection points.

Another form of the present technology comprises a positioning and stabilising structure for a patient interface, the positioning and stabilising structure comprising an integrally formed knitted strap that comprises multiple knitting structures, each knitting structure comprising different mechanical properties. The strap may be formed by flat knitting.

Another form of the present technology comprises a positioning and stabilising structure for a patient interface, the positioning and stabilising structure comprising an integrally formed knitted strap comprising at least a first portion and a second portion, the first portion having a different elasticity to the second portion. The first portion may comprise a ring strap portion configured to lie against posterior and superior surfaces of the patient's head. The second portion may comprise upper strap portions configured to lie alongside the patient's face in use and connect between the ring strap portion and a plenum chamber of the patient interface. The strap may be formed by flat knitting.

Another form of the present technology comprises a positioning and stabilising structure for a patient interface, the positioning and stabilising structure comprising an integrally formed knitted strap having a plurality of ventilation portions forming regions of increased breathability. The ventilation portions may comprise a first knitting structure and other portions of the strap may comprise a second knitting structure different from the first knitting structure. The ventilation portions may be formed with a pique mesh knitting structure while other portions of the strap may be formed with a single jersey or double jersey knitting structure. The strap may be formed by flat knitting.

Another form of the present technology comprises a positioning and stabilising structure for a patient interface, the positioning and stabilising structure comprising a strap comprising a ring strap portion configured to lie against posterior and superior surfaces of a patient's head and define a loop having an inside periphery, the ring strap portion comprising a rigidised portion at or proximate the inside periphery of the loop. The rigidised portion may comprise a first knitting structure and other portions of the ring strap portion may comprise a second knitting structure. The rigidised portion may comprise a pique knitting structure while other portions of the strap may comprise a single jersey or double jersey knitting structure. The strap may be formed by flat knitting.

Another form of the present technology comprises a positioning and stabilising structure for a patient interface, the positioning and stabilising structure comprising a strap comprising a fastening portion configured to be looped back and secured to itself to secure the strap to a frame or plenum chamber of the patient interface, the strap comprising a blind guide configured to provide a tactile indication of the location of the fastening portion of the strap. The strap may be an integrally formed with the blind guide. The strap may be formed by flat knitting.

Another form of the present technology comprises a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the patient interface comprising: 1) a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient; 2) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; 3) a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and 4) a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

In examples: a) the positioning and stabilising structure may comprise: 1) a ring strap portion having a superior portion configured to overlay the parietal bones of the patient's head in use and having an inferior portion configured to overlay or lie inferior to the occipital bone of the patient's head in use, the ring strap portion defining a loop; and 2) a pair of upper strap portions, each configured to connect between the ring strap portion and the cushion assembly in use on a respective side of the patient's head superior to an otobasion superior; b) the ring strap portion comprises a rigidised portion provided along a length of the loop defined by the ring strap portion.

In further examples: a) the rigidised portion is provided substantially along the entire length of the loop defined by the ring strap portion; b) the rigidised portion is provided to the ring strap portion proximate an inside periphery of the ring strap portion; c) the rigidised portion defines at least a portion of the inside periphery of the ring strap portion; d) the rigidised portion forms substantially the entire inside periphery of the ring strap portion; e) the rigidised portion is provided substantially centrally between an inside periphery of the ring strap portion and an outside periphery of the ring strap portion; f) the upper strap portions are stretchable; g) the rigidised portion is substantially non-stretchable; h) the ring strap portion comprises rounded edges; i) the rigidised portion comprises an increased material thickness relative to adjacent portions of the ring strap portion; j) a patient-contacting side of the ring strap portion is substantially flat and the increased material thickness is provided to a non-patient-contacting side of the ring strap portion; k) the ring strap portion comprises a thickness of 4 mm in the rigidised portion; l) the ring strap portion comprises a thickness of 2.5 mm in regions of the ring strap portion other than the rigidised portion; m) the rigidised portion is larger in regions of the ring strap portion proximate the upper strap portions than in other regions of the ring strap portion; and/or n) the rigidised portion is wider proximate the upper strap portions than in other regions of the ring strap portion.

In further examples: a) the ring strap portion comprises at least one ventilation portion structured and/or arranged to provide increased breathability through the ring strap portion at the ventilation portion; b) the ventilation portion comprises a knitted fabric having a pique mesh knitting structure; c) the ventilation portion is less stretchable than other portions of the ring strap portion; d) the rigidised portion surrounds the ventilation portion; e) the ring strap portion comprises a pair of superior ventilation portions, each provided proximate a respective upper strap portion; f) the rigidised portion surrounds each of the superior ventilation portions; g) the rigidised portion comprises a higher material thickness on a posterior side of each of the superior ventilation portions than on an anterior side of each of the superior ventilation portions; h) the positioning and stabilising structure comprises a pair of lower strap portions, each lower strap portion configured to connect between the ring strap portion and the cushion assembly in use on a respective side of the patient's head inferior to the otobasion superior; i) the ring strap portion comprises an inferior ventilation portion provided between the pair of lower strap portions; j) the inferior ventilation portion comprises an inferior edge spaced from an inferior edge of the ring strap portion; k) the inferior edge of the inferior ventilation portion comprises a greater curvature than the inferior edge of the ring strap portion to create a maximum spacing between the inferior edge of the inferior ventilation portion and the inferior edge of the ring strap portion at or proximate the sagittal plane of the patient's head in use; l) the lower strap portions are stretchable; m) the ring strap portion comprises a knitted fabric structure; n) the ring strap portion is formed by flat knitting; o) the ring strap portion comprises a single jersey knitting structure; p) the ring strap portion comprises a double jersey loop formation knitting structure; q) the rigidised portion comprises a pique knitting structure; r) the superior portion of the ring strap portion comprises a pair of overhead strap portions adjustably connected to each other proximate the sagittal plane of the patient's head; s) the overhead strap portions are adjustably connected with a buckle; t) the overhead strap portions comprise hook and loop fastening material to allow each of the overhead strap portions to be passed through a portion of the buckle and secured back onto itself; u) the positioning and stabilising structure comprises a frame coupled to the plenum chamber, the upper strap portions being configured to connect to the frame; and/or v) the positioning and stabilising structure further comprises lower strap portions configured to connect to the frame.

Another form of the present technology comprises a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing, the patient interface comprising: 1) a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; 2) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; 3) a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and 4) a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

In examples: a) the positioning and stabilising structure comprises at least one strap configured to connect to the cushion assembly, the strap being formed from a knitted fabric and comprising a fastening portion proximate an end of the strap, the fastening portion being structured and/or arranged to allow the strap to be looped back and fastened onto itself to connect to the cushion assembly; b) the strap comprises at least one blind guide formed by the knitted fabric and configured to provide a tactile indication of the location of the fastening portion on the strap.

In further examples: a) the strap is formed by flat knitting; b) the strap comprises a non-patient-contacting surface and the at least one blind guide comprises a raised portion being raised with respect to the non-patient-contacting surface and/or a recessed portion being recessed with respect to the non-patient-contacting surface; c) the raised portion and/or the recessed portion surrounds at least part of the fastening portion of the strap; d) the raised portion comprises an elongate raised profile on the non-patient-contacting surface of the strap; e) the elongate raised profile is provided at one or more edges of the fastening portion; f) the elongate raised profile is provided at edges of the fastening portion which in use are superior, posterior and inferior edges; g) the elongate raised profile comprises a rounded raised surface; h) the raised portion is formed by an increased thickness of the strap in comparison to adjacent regions of the strap, and the recessed portion is formed by a decreased thickness of the strap in comparison to adjacent regions of the strap; i) the fastening portion of the strap comprises a hook-and-loop fastening material; j) the fastening portion comprises an end portion comprising one of a hook material and a loop material provided to the non-patient-contacting surface and an intermediate portion comprising the other of the hook material and the loop material provided to the non-patient-contacting surface; k) the intermediate portion is longer than the end portion. The intermediate portion may be several times longer than the end portion; l) the strap and the blind guide are formed during a single knitting process; m) the blind guide comprises a pique knitting structure; n) the strap comprises a single jersey knitting structure; o) the strap comprises a double jersey loop formation; p) the strap connects to the cushion assembly via a frame of the patient interface; q) the strap comprises: a ring strap portion having a superior portion configured to lie against the patient's head over the parietal bones of the patient's head in use and having an inferior portion configured to lie against the patient's head over or inferior to the occipital bones of the patient's head in use; and a pair of upper strap portions, each configured to connect between the ring strap portion and the cushion assembly in use on a respective side of the patient's head superior to an otobasion superior; r) the strap comprises a pair of lower strap portions, each lower strap portion being configured to connect between the ring strap portion and the cushion assembly in use on a respective side of the patient's head inferior to the otobasion superior; and/or s) the strap and the blind guide are integrally formed.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; the patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; 2) a seal-forming structure having a textile membrane constructed and arranged to form a pressure-assisted seal with a region of the patient's face surrounding an entrance to the patient's airways inferior to a nasal bridge region of the patient's face, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use; and 3) a positioning and stabilising structure to provide a force to hold the seal-forming structure in a therapeutically effective position on the patient's head, the positioning and stabilising structure being constructed and arranged so that at least a portion overlies a region of the patient's head superior to an otobasion superior of the patient's head in use.

In examples: a) the positioning and stabilizing structure comprises a one-piece knitted headgear strap of a single piece of material; b) the knitted headgear strap includes at least one first area having a first knit structure; c) the knitted headgear strap includes at least one second area having a second mesh knit structure forming at least one ventilation area having increased flexibility as compared to the first area; and d) the knitted headgear strap includes at least one third area having a rigidized knit structure directly adjacent the at least one ventilation area, the rigidized knit structure having increased rigidity as compared to the first knit structure and the second mesh knit structure.

In further examples: a) the rigidized knit structure surrounds the at least one ventilation area; b) the rigidized knit structure is a pique knit structure; c) the pique knit structure is a pique rib structure; d) the second mesh knit structure is a pique mesh knit structure; e) the ventilation areas have increased breathability as compared to the at least one first area and the at least one third area.

In further examples: a) the knitted headgear strap comprises a ring strap portion having a superior portion configured to overlay the parietal bones of the patient's head in use and having an inferior portion configured to overlay or lie inferior to the occipital bone of the patient's head in use, the ring strap portion defining a loop; b) the ring strap portion has an inner edge and an outer edge, and the rigidized knit structure extends along the inner edge of the ring strap portion; c) the rigidized knit structure forms a loop extending along the entire inner edge of the ring strap portion; d) the ring strap portion includes the at least one ventilation area; e) the knitted headgear strap further comprises a neck strap portion configured to overlay the occipital bone of the patient's head and/or lie against the patient's neck in use, and the neck strap portion includes the at least one ventilation area; the first knit structure is a jersey knit structure.

Another aspect of the present technology relates to a patient interface for sealed delivery of a flow of air at a continuously positive pressure with respect to ambient air pressure to an entrance to a patient's airways including at least entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; the patient interface comprising: 1) a plenum chamber at least partially forming a cavity pressurisable to a therapeutic pressure of at least 6 cmH$_2$O above ambient air pressure, said plenum chamber including a plenum chamber inlet port sized and structured to receive a flow of air at the therapeutic pressure for breathing by a patient; 2) a seal-forming structure having a textile membrane constructed and arranged to form a pressure-assisted seal with a region of the patient's face surrounding an entrance to the patient's airways inferior to a nasal bridge region of the patient's face, said textile membrane having a hole formed therein such that the flow of air at said therapeutic pressure is delivered to at least an entrance to the patient's nares, the seal-forming structure constructed and arranged to maintain said therapeutic pressure in the cavity throughout the patient's respiratory cycle in use; and 3) a positioning and stabilising structure to provide a force to hold the seal-forming structure in a therapeutically effective position on the patient's head, the positioning and stabilising structure being constructed and arranged so that at least a portion overlies a region of the patient's head superior to an otobasion superior of the patient's head in use.

In examples: a) the positioning and stabilizing structure comprises a one-piece knitted headgear strap of a single piece of material; b) the knitted headgear strap includes a first area having a first knit structure; c) the knitted headgear strap includes a second area having a second pique knit structure, the second pique knit structure having increased rigidity as compared to the first knit structure; d) the second pique knit structure extends along a first edge of the knitted headgear strap and is directly adjacent the first knit structure.

In further examples: a) the first knit structure extends along a second edge of the knitted headgear strap; b) the knitted headgear strap comprises a ring strap portion having a superior portion configured to overlay the parietal bones of the patient's head in use and having an inferior portion configured to overlay or lie inferior to the occipital bone of the patient's head in use, the ring strap portion defining a loop; c) the ring strap portion has an inner edge and an outer edge, and the first edge of the knitted headgear strap forms the inner edge of the ring strap portion; d) the first knit structure extends along a second edge of the knitted headgear strap, and the second edge of the knitted headgear strap forms the outer edge of the ring strap portion.

In further examples: a) the first knit structure has increased stretchability as compared to the second pique knit structure; b) the knitted headgear strap further includes a third area having a third mesh knit structure, the third mesh knit structure being less rigid than the first knit structure and the second pique knit structure; c) the third mesh knit structure is a pique mesh knit structure; d) the second pique knit structure extend directly adjacent the third mesh knit structure; e) the third mesh knit structure forms a ventilation area having increased breathability as compared to the first area and the second area, the second pique knit structure surrounding the ventilation area; the first knit structure is a jersey knit structure.

Another aspect of the present technology relates to a method of forming a positioning and stabilising structure for a patient interface, the a positioning and stabilising structure being configured to provide a force to hold a seal-forming structure in a therapeutically effective position on a patient's head for the treatment of sleep disordered breathing, the method comprising: knitting a one-piece headgear strap as a single piece of material directly into its final shape.

In further examples: a) the step of knitting the one-piece headgear strap includes knitting at least one first area of the headgear strap having a first knit structure; b) the step of knitting the one-piece headgear strap includes knitting at least one second area of the headgear strap having a second mesh knit structure forming at least one ventilation area of the headgear strap having increased flexibility as compared to the first area; c) the step of knitting the one-piece headgear strap includes knitting at least one third area of the headgear strap having a rigidized knit structure directly adjacent the at least one ventilation area, the rigidized knit structure having increased rigidity as compared to the first knit structure and the second mesh knit structure; d) the headgear strap includes a plurality of strap portions configured to connect to a cushion assembly to hold the seal-forming structure in the therapeutically effective position on a patient's head in use.

In further examples: a) the step of knitting the one-piece headgear strap comprises a single flat knitting process; b) the rigidized knit structure surrounds the at least one ventilation area; c) the rigidized knit structure is a pique knit structure; d) the second mesh knit structure is a pique mesh knit structure e) the ventilation areas have increased breathability as compared to the at least one first area and the at least one third area; f) the knitted headgear strap comprises a ring strap portion having a superior portion configured to overlay the parietal bones of the patient's head in use and having an inferior portion configured to overlay or lie inferior to the occipital bone of the patient's head in use, the ring strap portion defining a loop; g) the ring strap portion has an inner edge and an outer edge, and the rigidized knit structure extends along the inner edge of the ring strap portion; h) the rigidized knit structure forms a loop extending along the entire inner edge of the ring strap portion; i) the first knit structure is a jersey knit structure.

Another form of the present technology comprises a patient interface comprising: 1) a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; 2) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; 3) a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and 4) a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

In examples: a) the positioning and stabilising structure comprises: 1) a pair of headgear conduits to receive the flow of air from a connection port on top of the patient's head and to deliver the flow of air to the entrance of the patient's airways via the seal-forming structure, each headgear conduit constructed and arranged to contact, in use, at least a region of the patient's head superior to an otobasion superior of the patient's head on a respective side of the patient's head; and 2) a strap integrally formed by flat knitting.

In further examples: a) the headgear strap comprises: 1) a neck strap portion configured to overlay the occipital bone of the patient's head and/or lie against the patient's neck in use; 2) a pair of upper strap portions, each configured to connect between the neck strap portion and a respective headgear conduit on a respective side of the patient's head; and 3) a pair of lower strap portions, each configured to connect between the neck strap portion and a respective headgear conduit.

In further examples: a) the strap is formed by a single flat knitting process; b) the strap comprises a rigidised portion; c) the rigidised portion comprises a pique knitting structure; d) the neck strap portion comprises the rigidised portion; e) the neck strap portion comprises one or more stretchable portions; f) the neck strap portion comprises a superior stretchable portion and an inferior stretchable portion; g) the superior stretchable portion is provided along a superior edge of the neck strap portion; h) the inferior stretchable portion is provided along an inferior edge of the neck strap portion; i) the strap comprises a ventilation portion structured and/or arranged to provide increased breathability through the strap at the ventilation portion; j) the ventilation portion is located in the neck strap portion; k) the ventilation portion comprises a knitted fabric having a pique mesh knitting structure; l) the ventilation portion is less stretchable than other portions of the ring strap portion; and/or m) the rigidised portion surrounds the ventilation portion.

In further examples: a) the strap comprises a fastening portion proximate an end of the strap, the fastening portion being structured and/or arranged to allow the strap to be looped back and fastened onto itself to connect to the plenum chamber, the strap comprising at least one blind guide formed by knitted fabric forming the integrally formed strap and configured to provide a tactile indication of the location of the fastening portion on the strap; b) the strap comprises a non-patient-contacting surface and the at least one blind guide comprises a raised portion, the raised portion being raised with respect to the non-patient-contacting surface; c) the raised portion comprises an elongate raised profile on the non-patient-contacting surface of the strap; d) the fastening portion of the strap comprises a hook-and-loop fastening material; and/or e) each of the upper strap portions and lower strap portions comprises a respective blind guide.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Another aspect of the present technology relates to a treatment system used for treatment of sleep disordered breathing, comprising: 1) the patient interface according to any of the above aspects; 2) a respiratory pressure therapy (RPT) device to supply breathable gas at positive pressure; and 3) an air delivery tube to pass the breathable gas from the RPT device to the patient interface.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
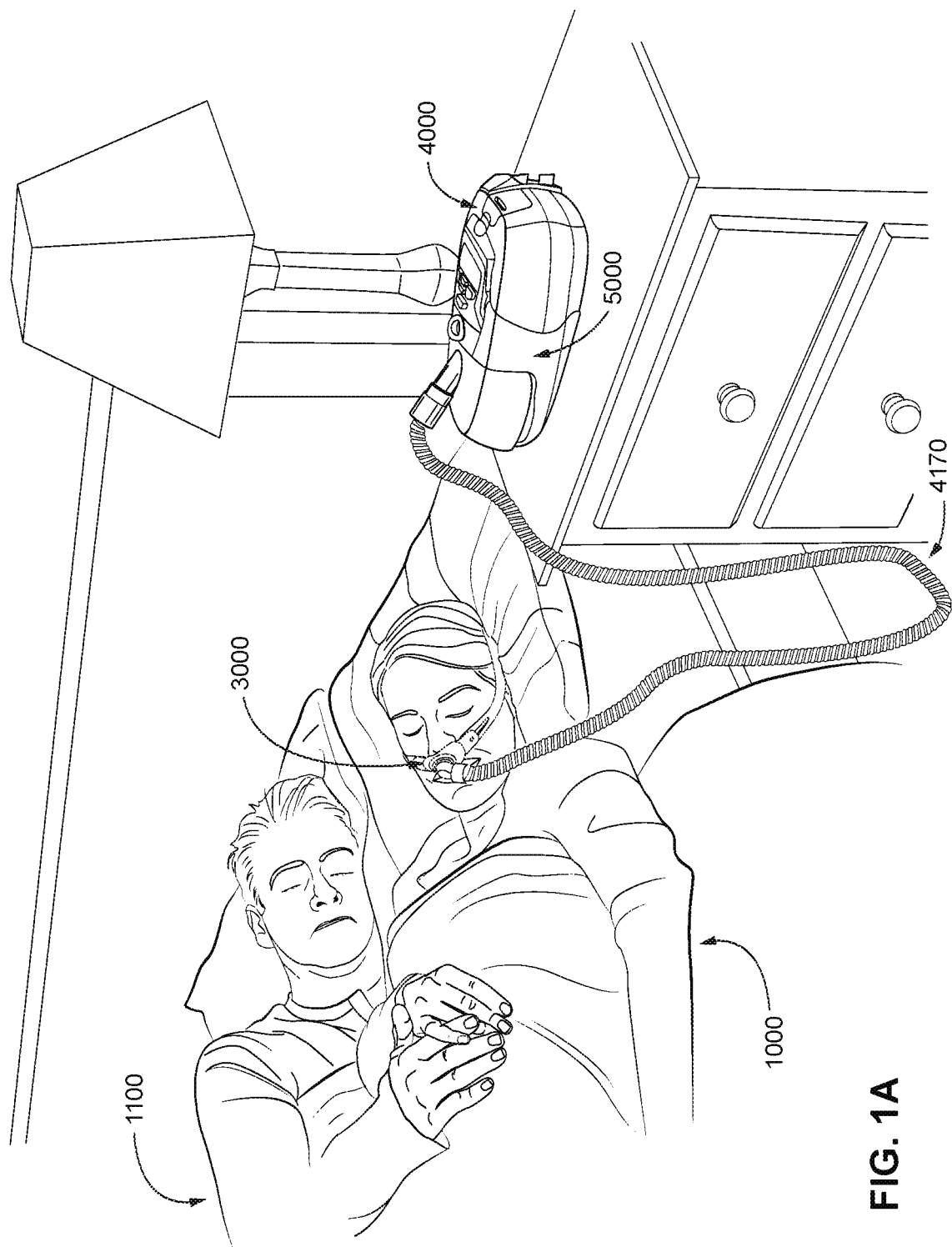
Figure 1B:
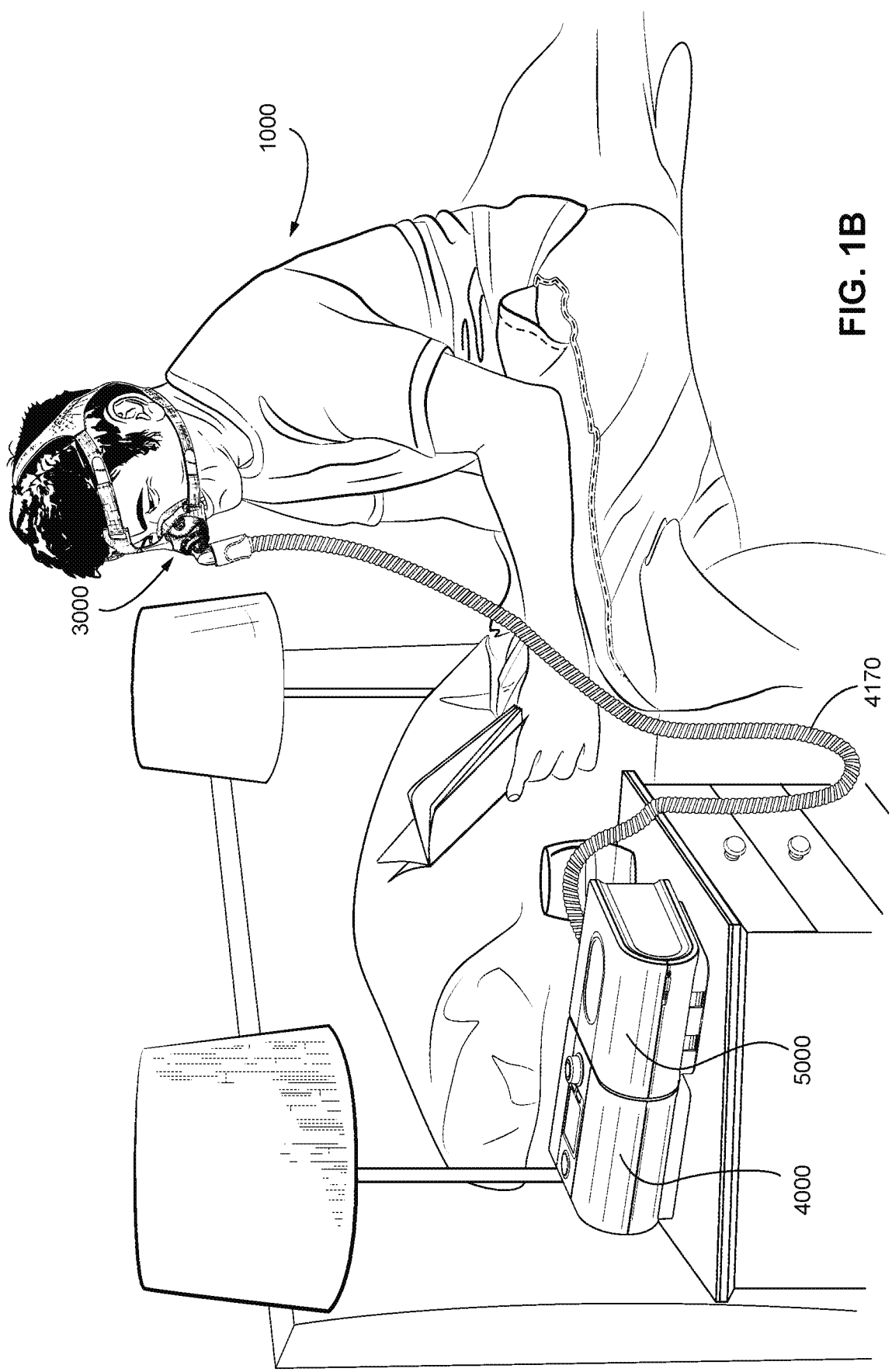
Figure 1C:
Figure 2A:
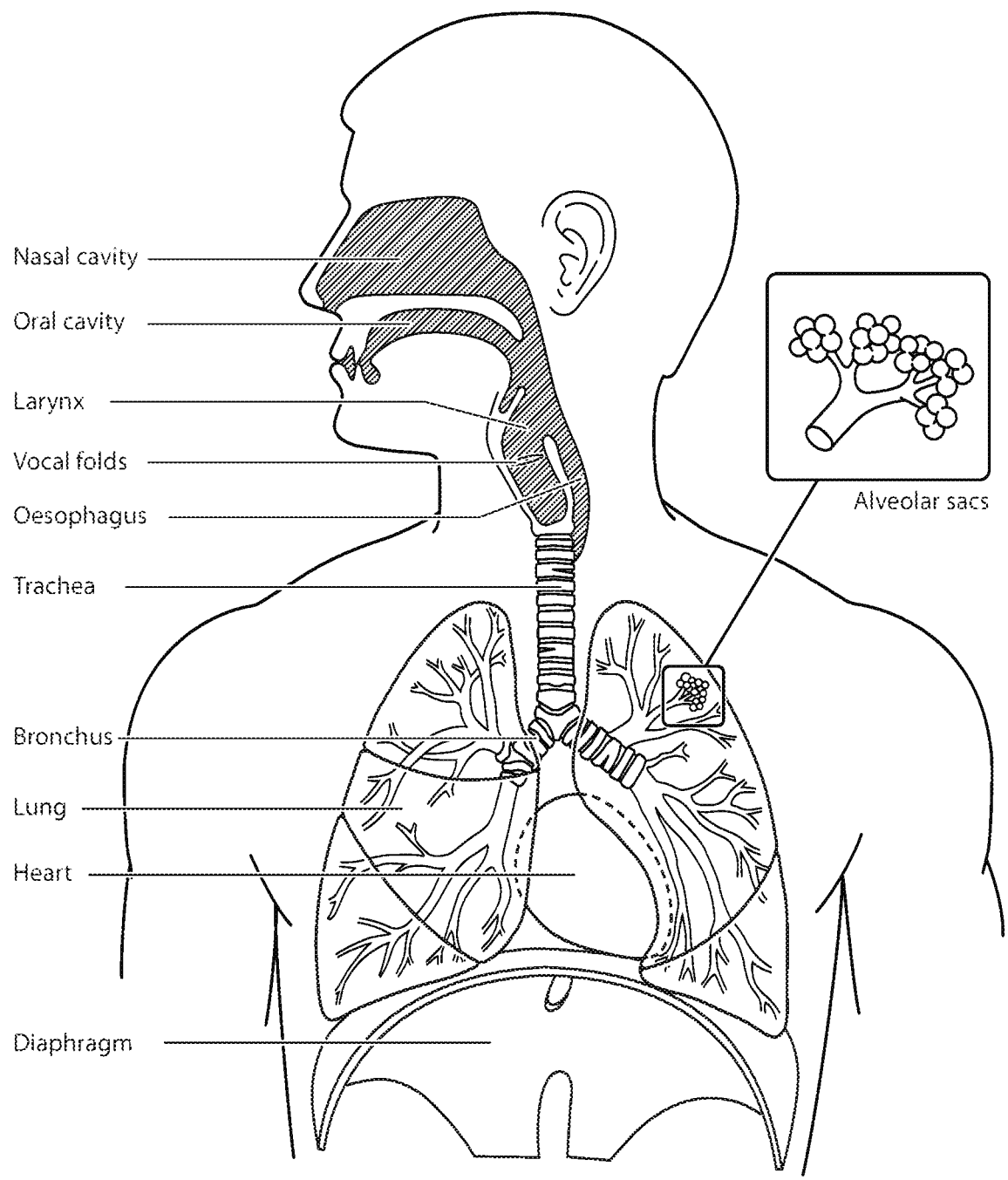
FIG. 2A shows an overview of a human respiratory system including the nasal and oral cavities, the larynx, vocal folds, oesophagus, trachea, bronchus, lung, alveolar sacs, heart and diaphragm.
Figure 2B:
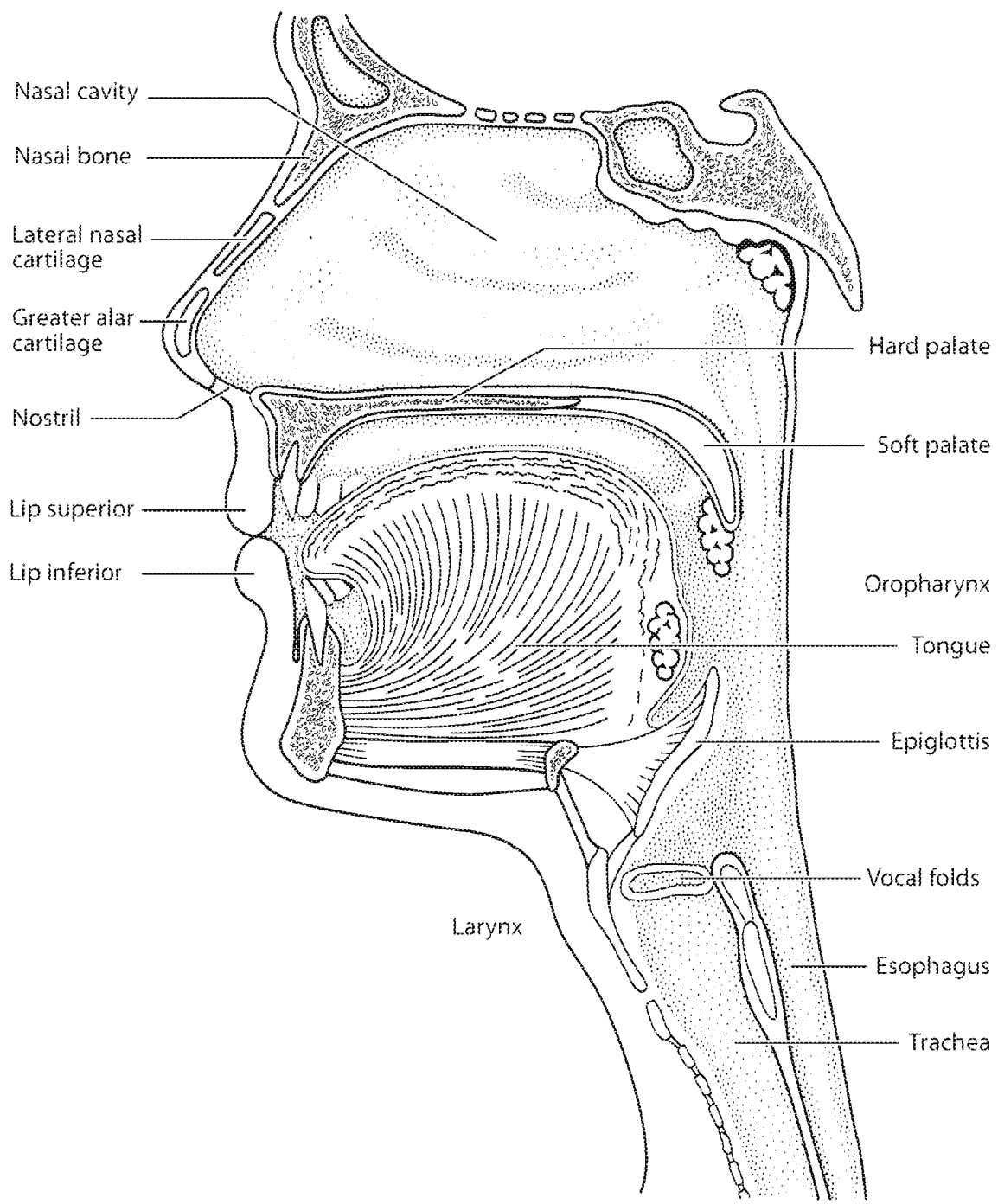
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
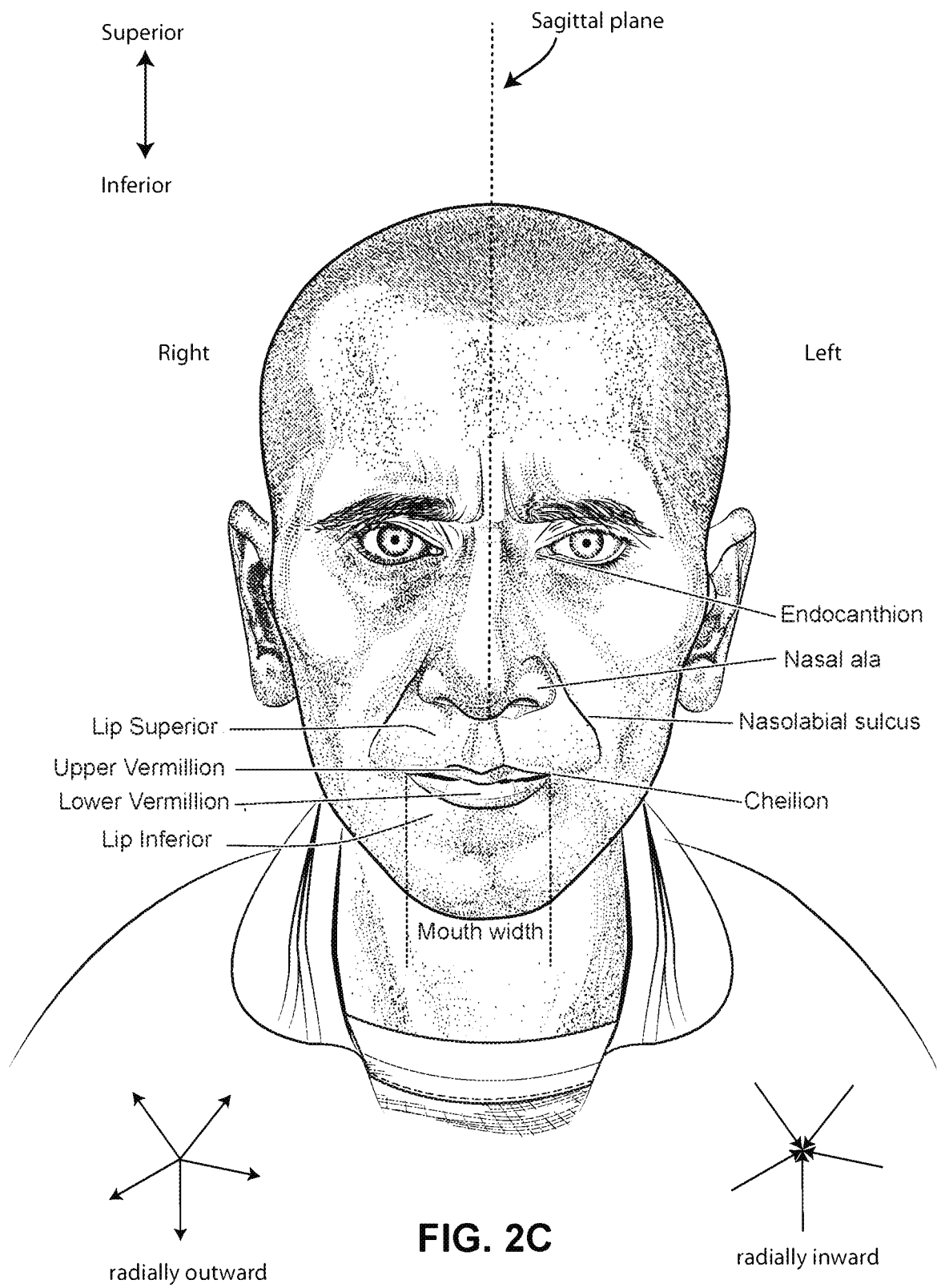
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
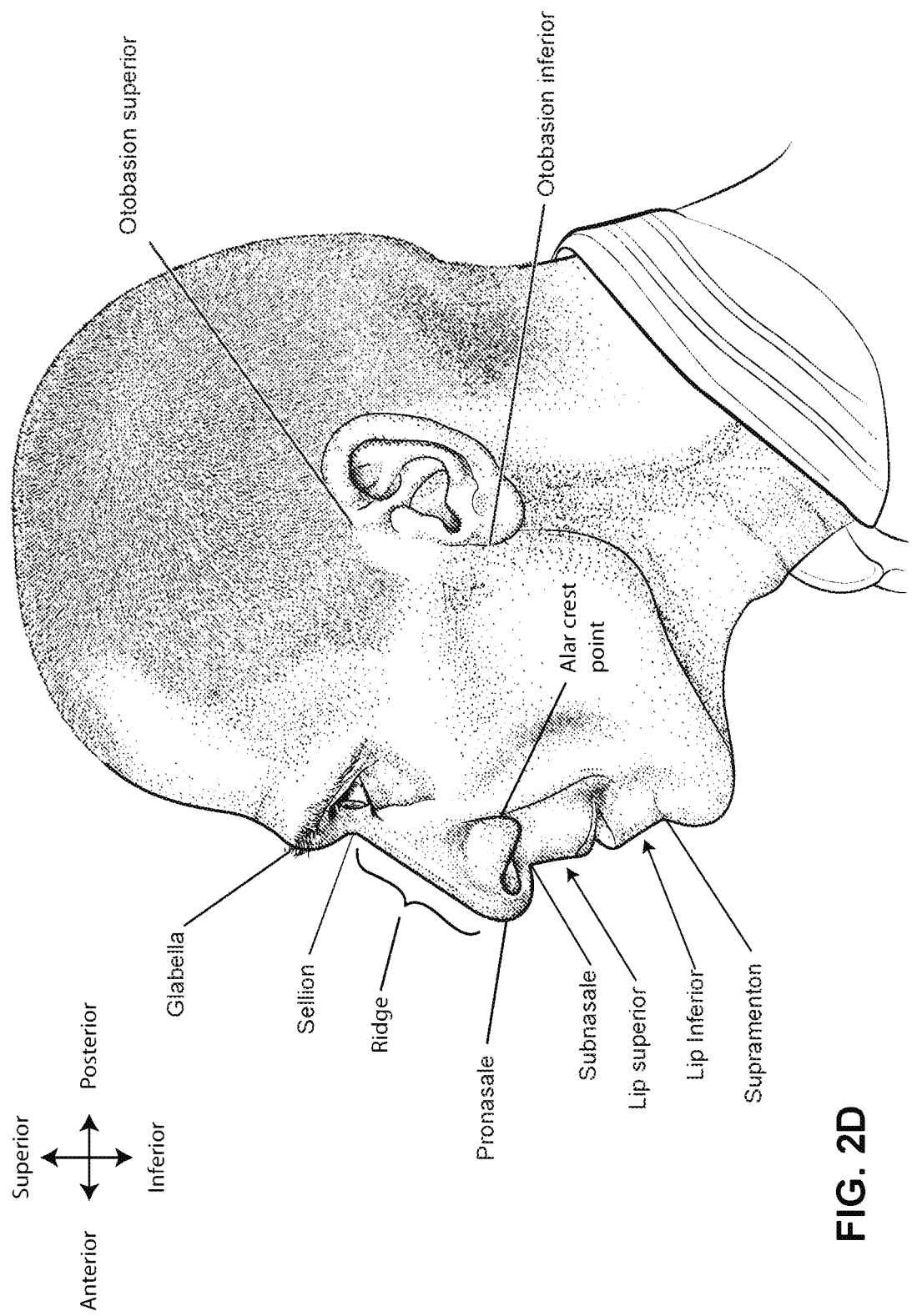
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
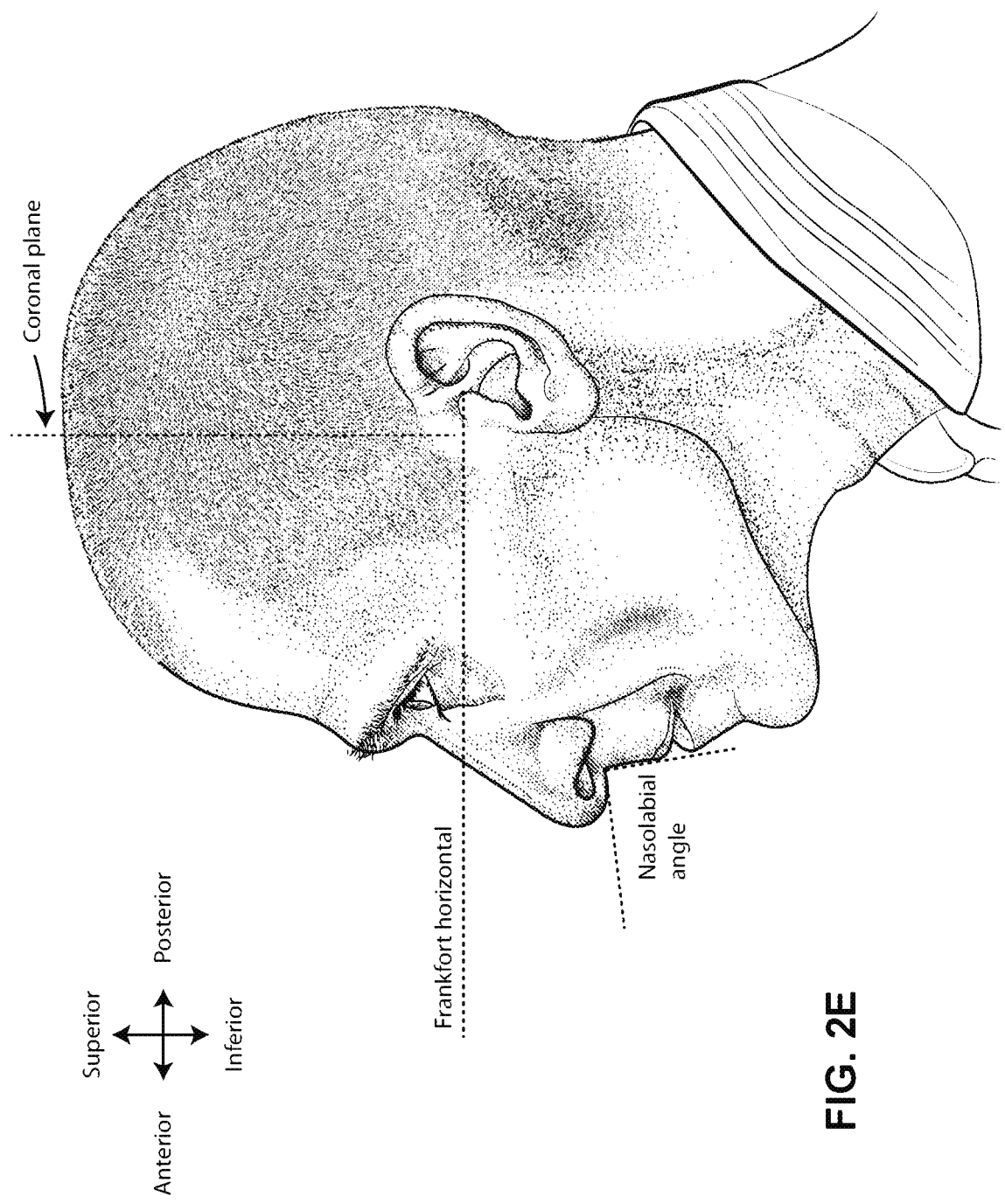

FIG. 2E is a further side view of a head. The approximate locations of the Frankfort horizontal and nasolabial angle are indicated. The coronal plane is also indicated.

Figure 2F:
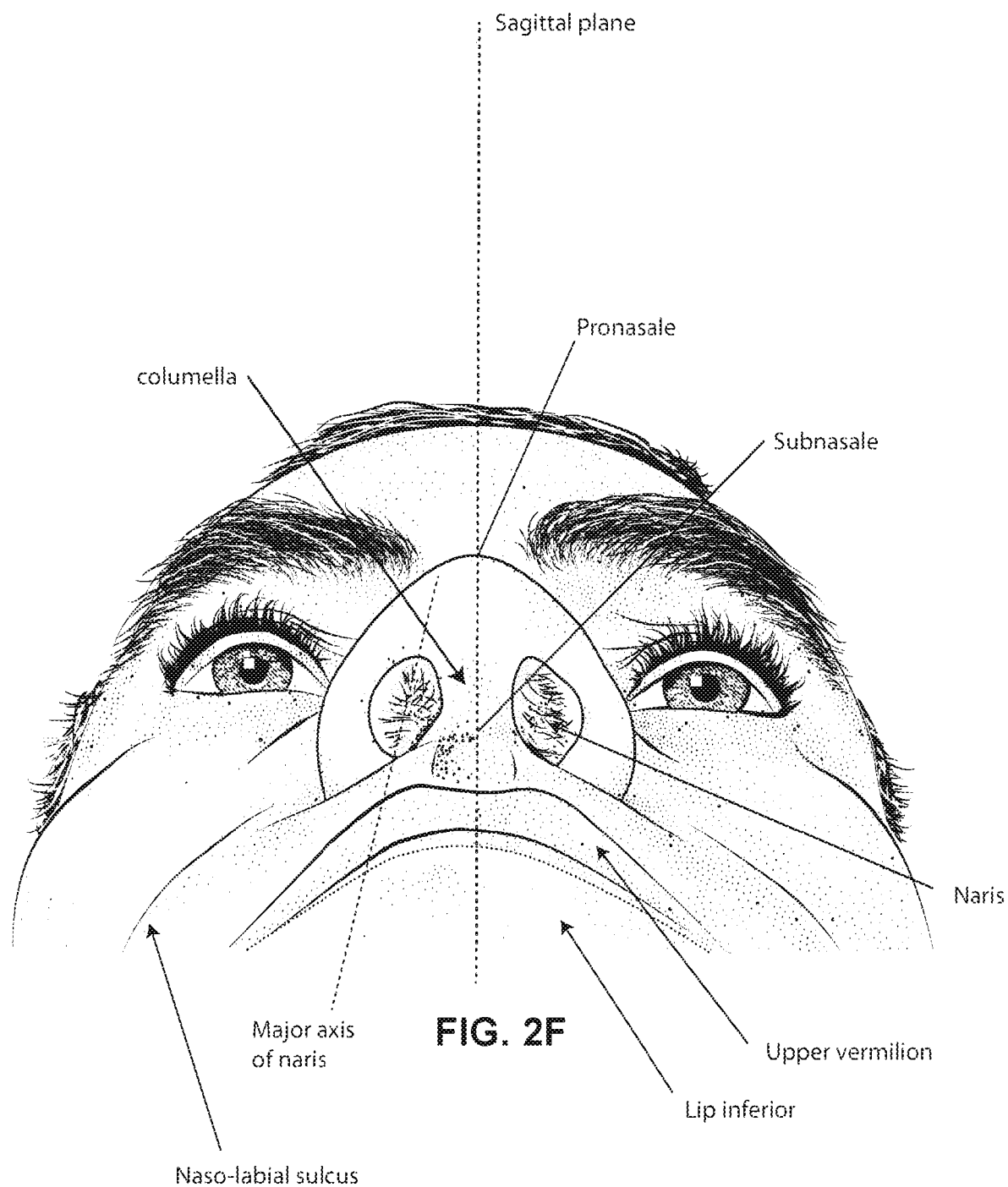

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
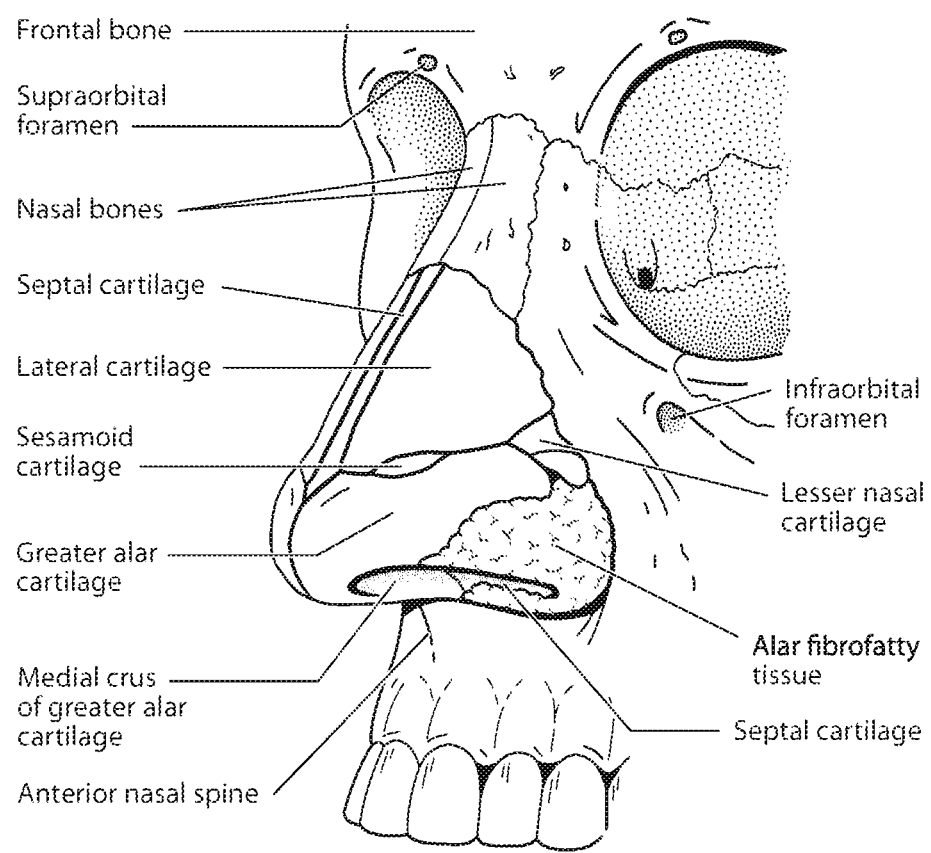

FIG. 2L shows an anterolateral view of a nose.

4.3 Patient Interface

Figure 3A:
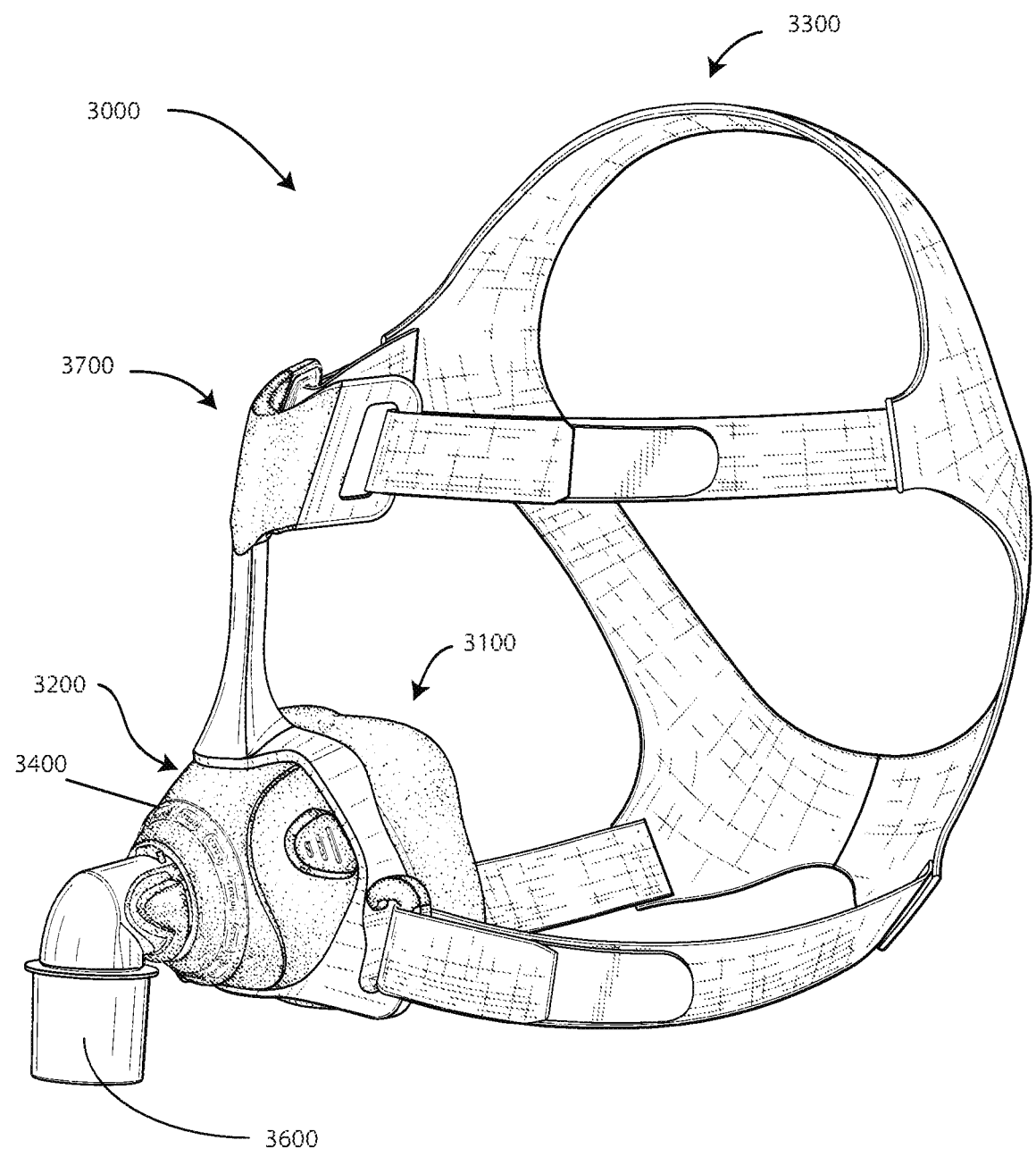

FIG. 3A shows a patient interface in the form of a nasal mask in accordance with one form of the present technology.

Figure 3B:
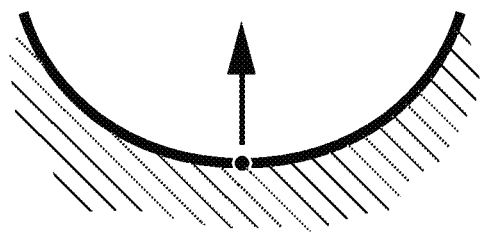

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
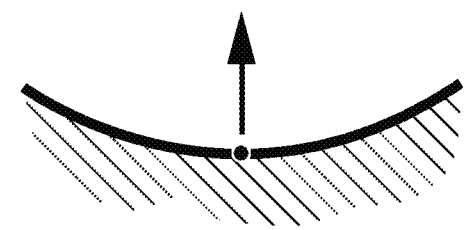

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
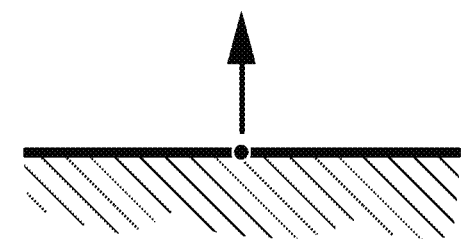

FIG. 3D shows a schematic of a cross-section through a structure at a point. An outward normal at the point is indicated. The curvature at the point has a value of zero.

Figure 3E:
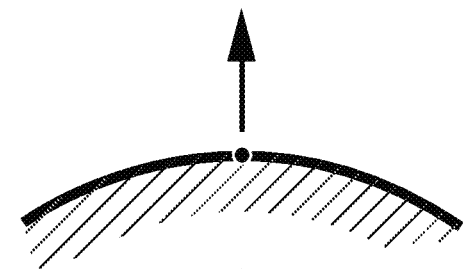

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
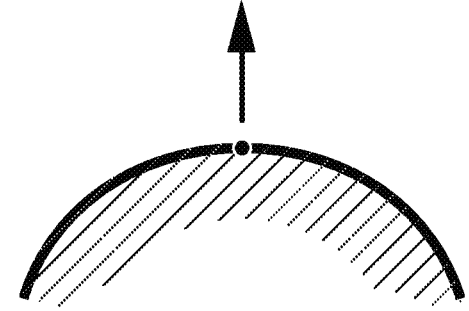

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
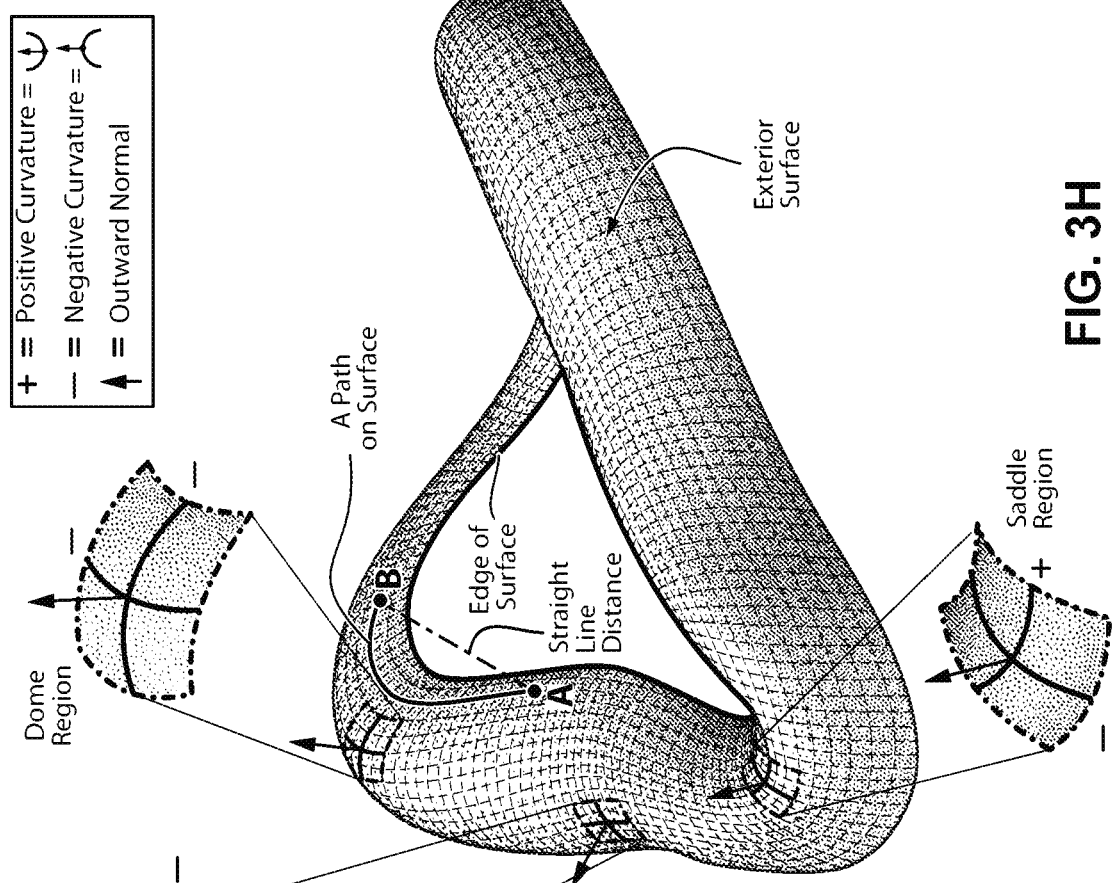
Figure 3G:
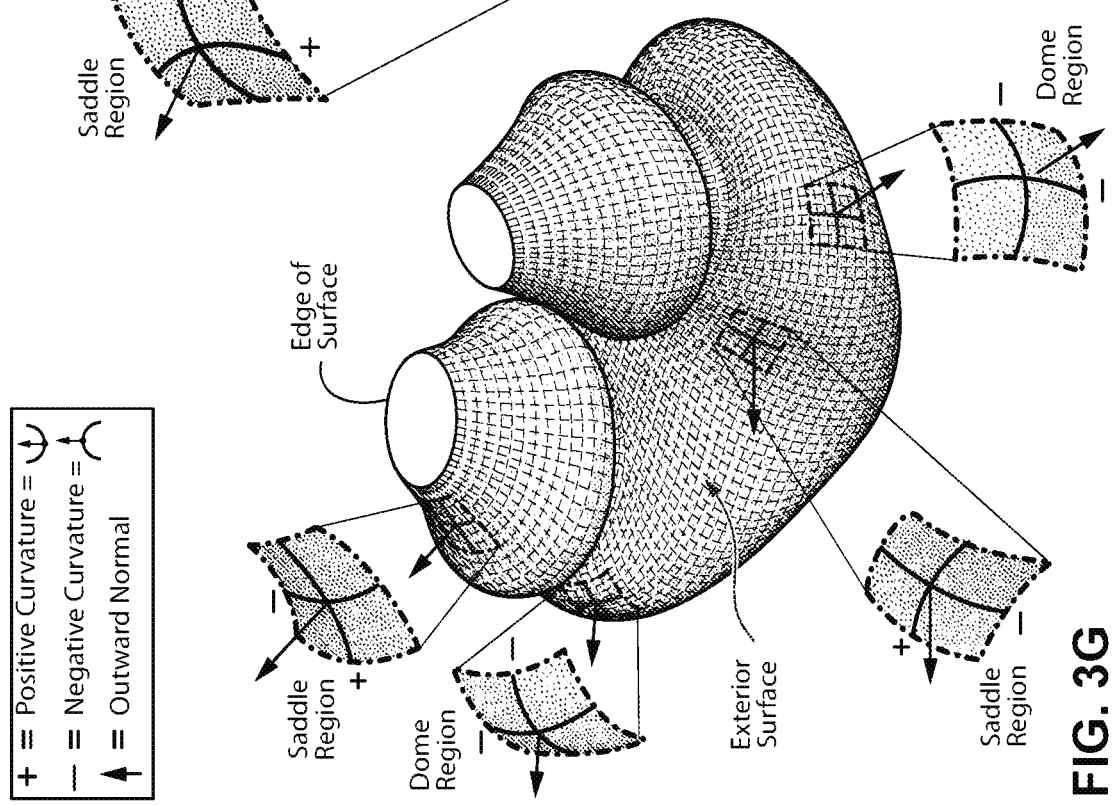

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
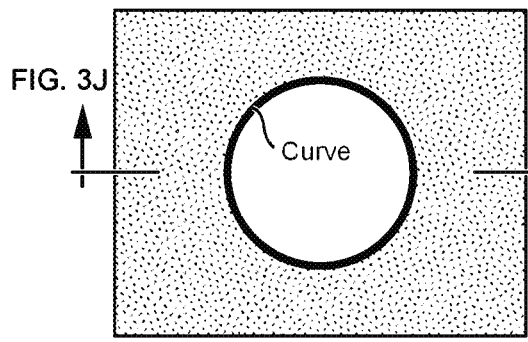

FIG. 3I shows the surface of a structure, with a one dimensional hole in the surface. The illustrated plane curve forms the boundary of a one dimensional hole.

Figure 3J:
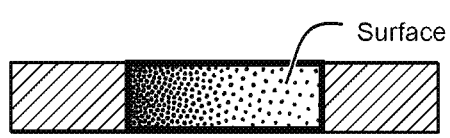

FIG. 3J shows a cross-section through the structure of FIG. 3I. The illustrated surface bounds a two dimensional hole in the structure of FIG. 3I.

Figure 3K:
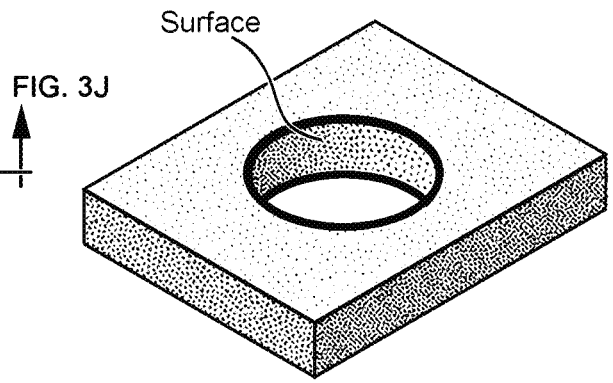

FIG. 3K shows a perspective view of the structure of FIG. 3I, including the two dimensional hole and the one dimensional hole. Also shown is the surface that bounds a two dimensional hole in the structure of FIG. 3I.

Figure 3L:
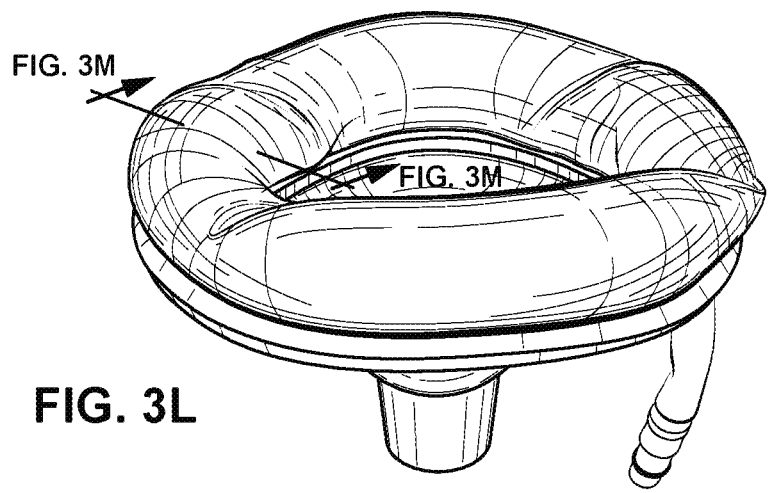

FIG. 3L shows a mask having an inflatable bladder as a cushion.

Figure 3M:
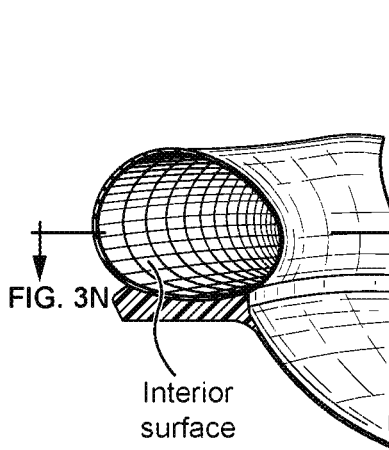

FIG. 3M shows a cross-section through the mask of FIG. 3L, and shows the interior surface of the bladder. The interior surface bounds the two dimensional hole in the mask.

Figure 3N:
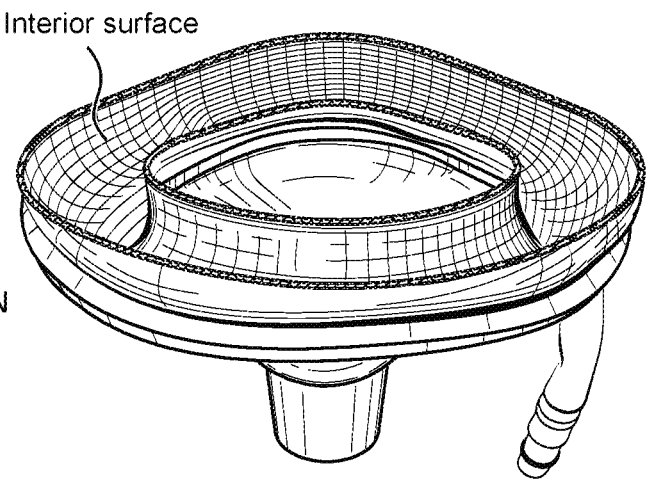

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
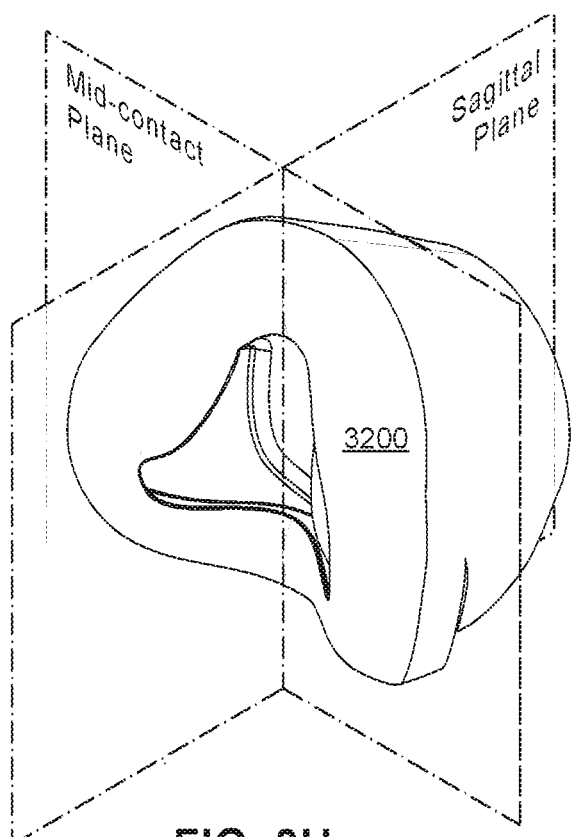

FIG. 3U shows a view of a plenum chamber 3200 showing a sagittal plane and a mid-contact plane.

Figure 3V:
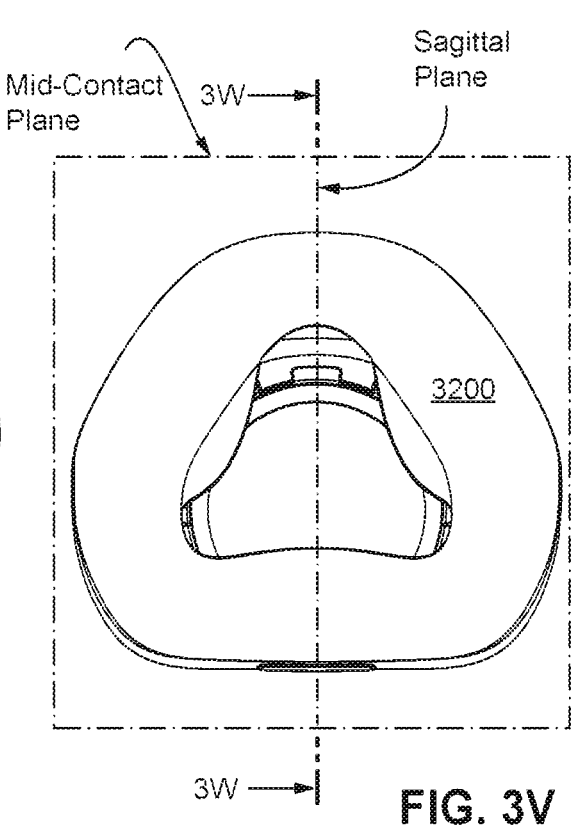

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
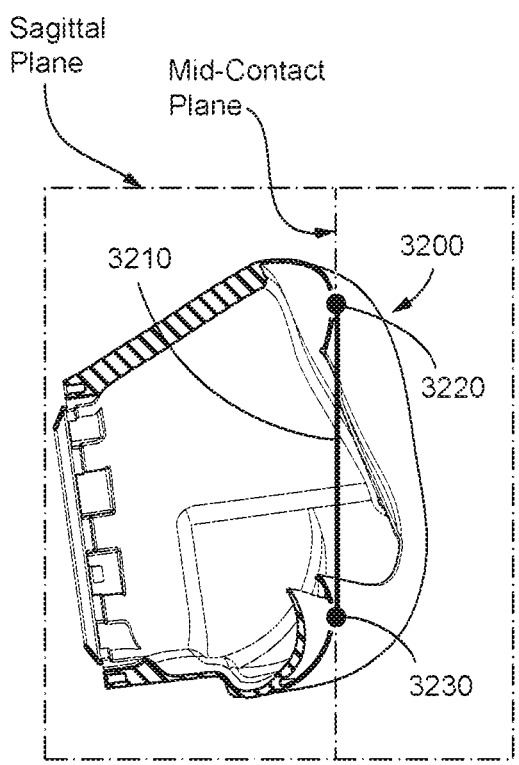

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
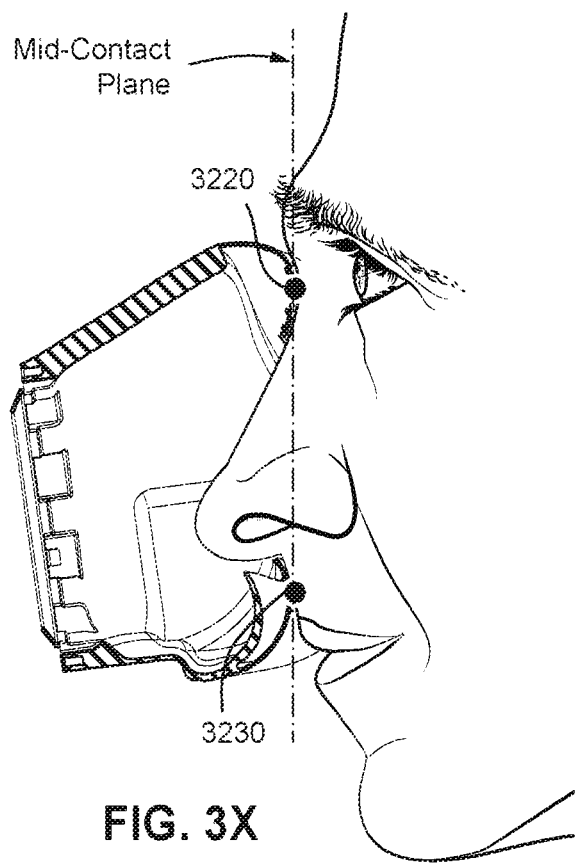

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
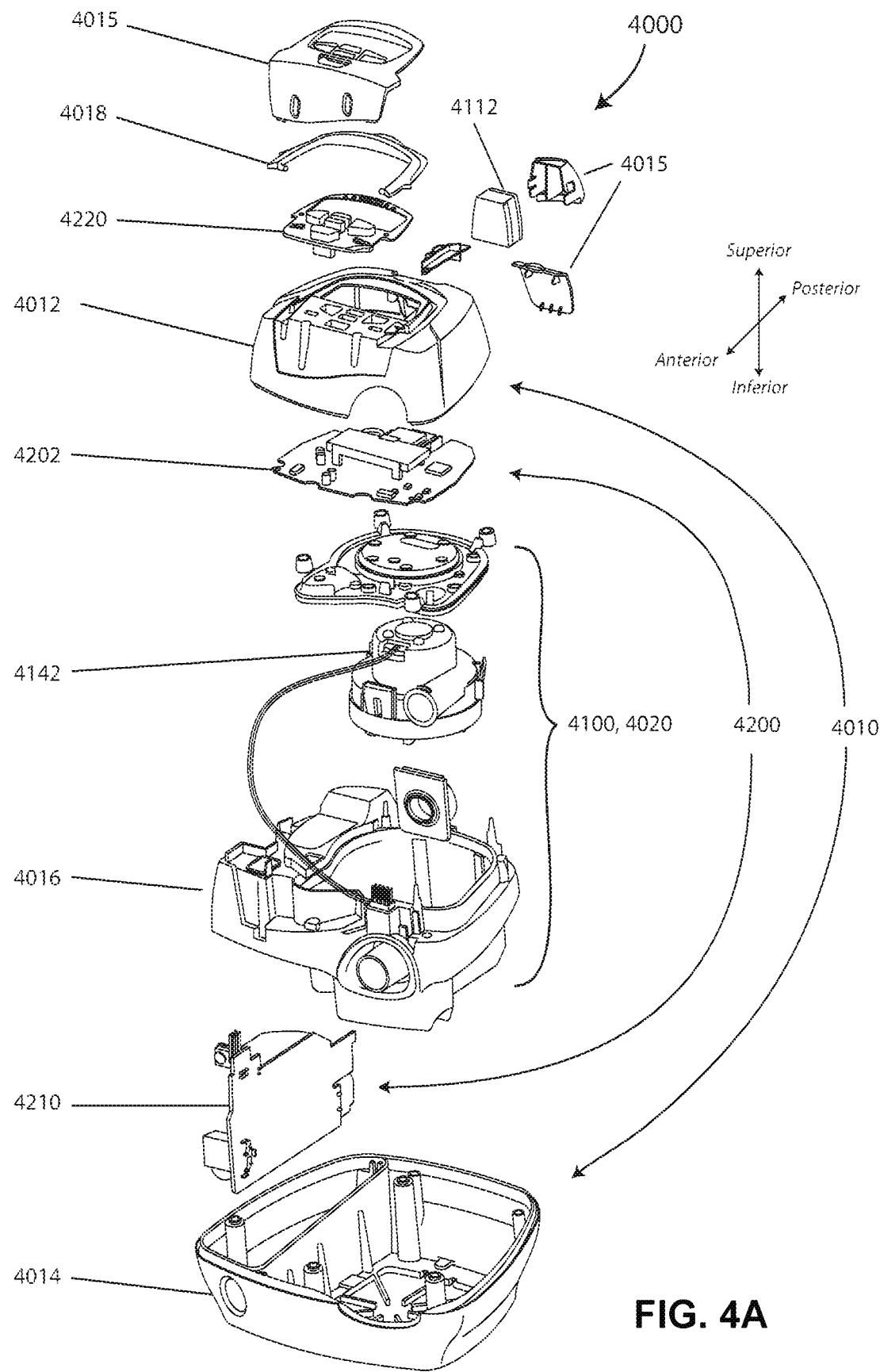

FIG. 4A shows an RPT device in accordance with one form of the present technology.

Figure 4B:
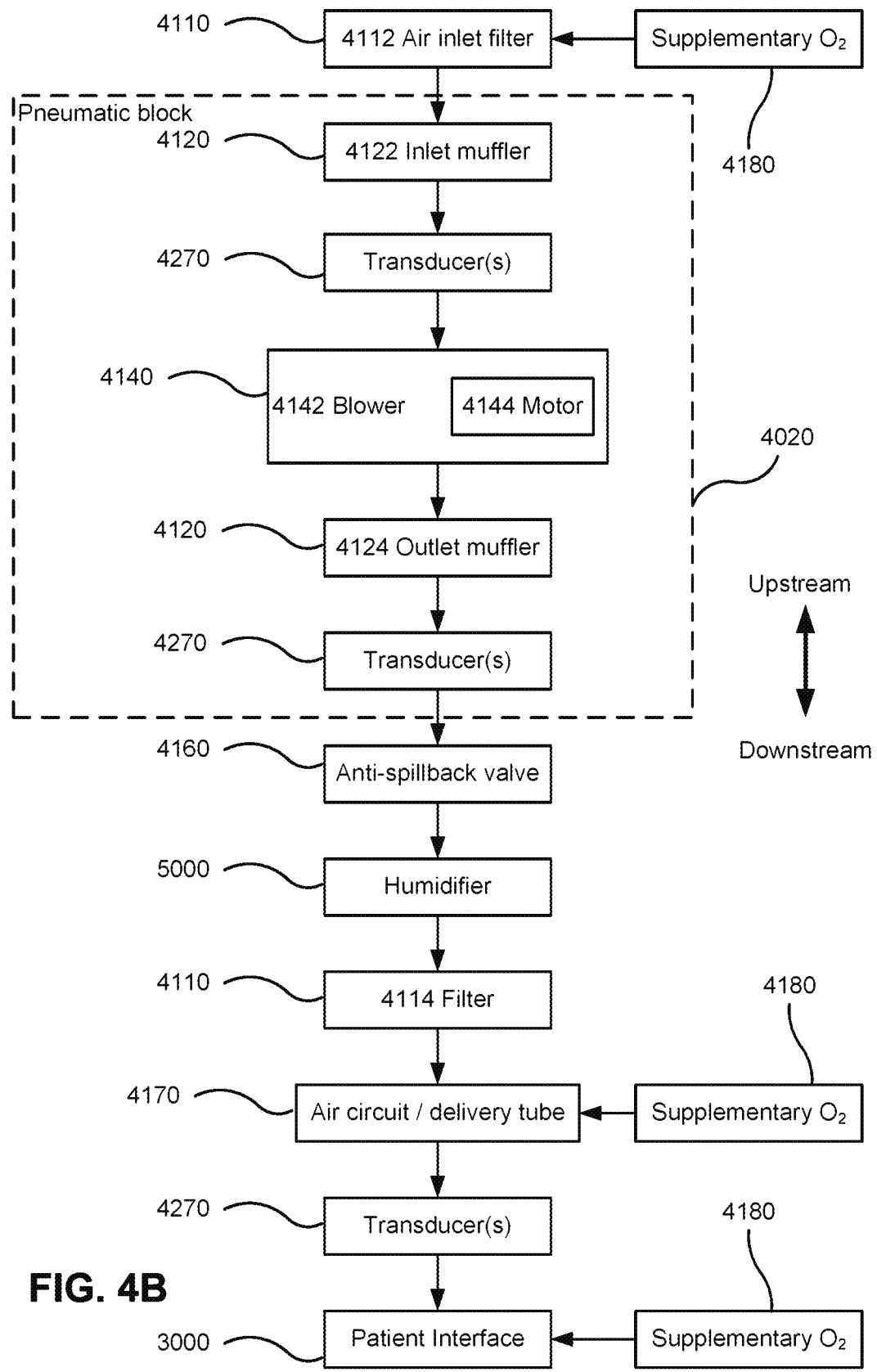

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
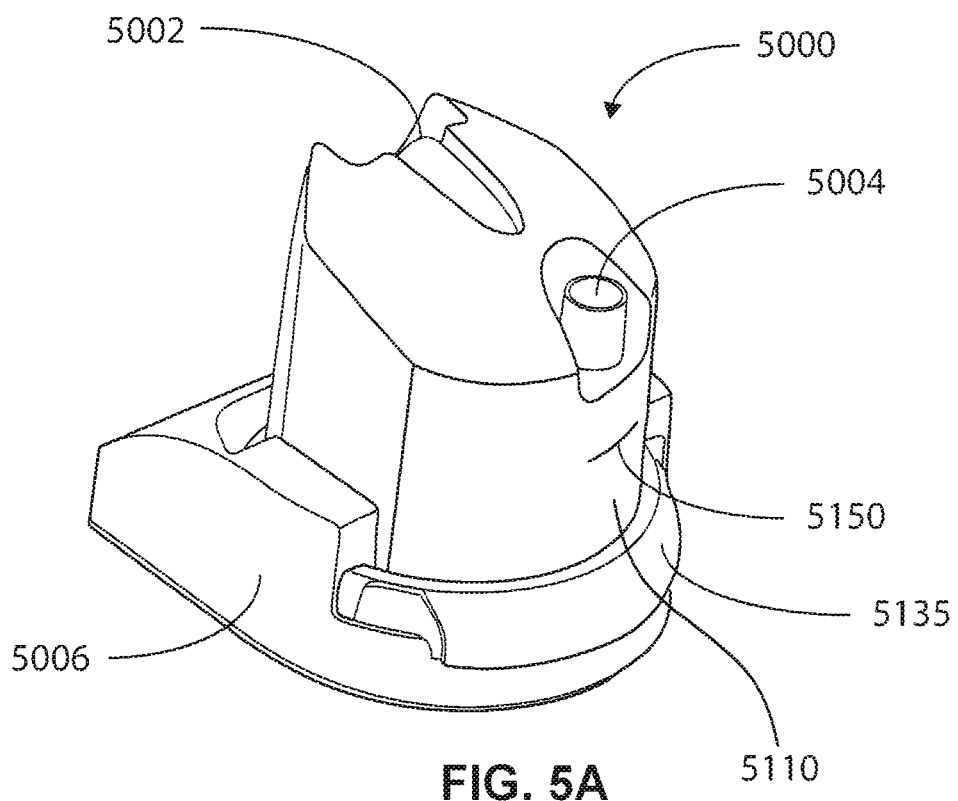

FIG. 5A shows an isometric view of a humidifier in accordance with one form of the present technology.

Figure 5B:
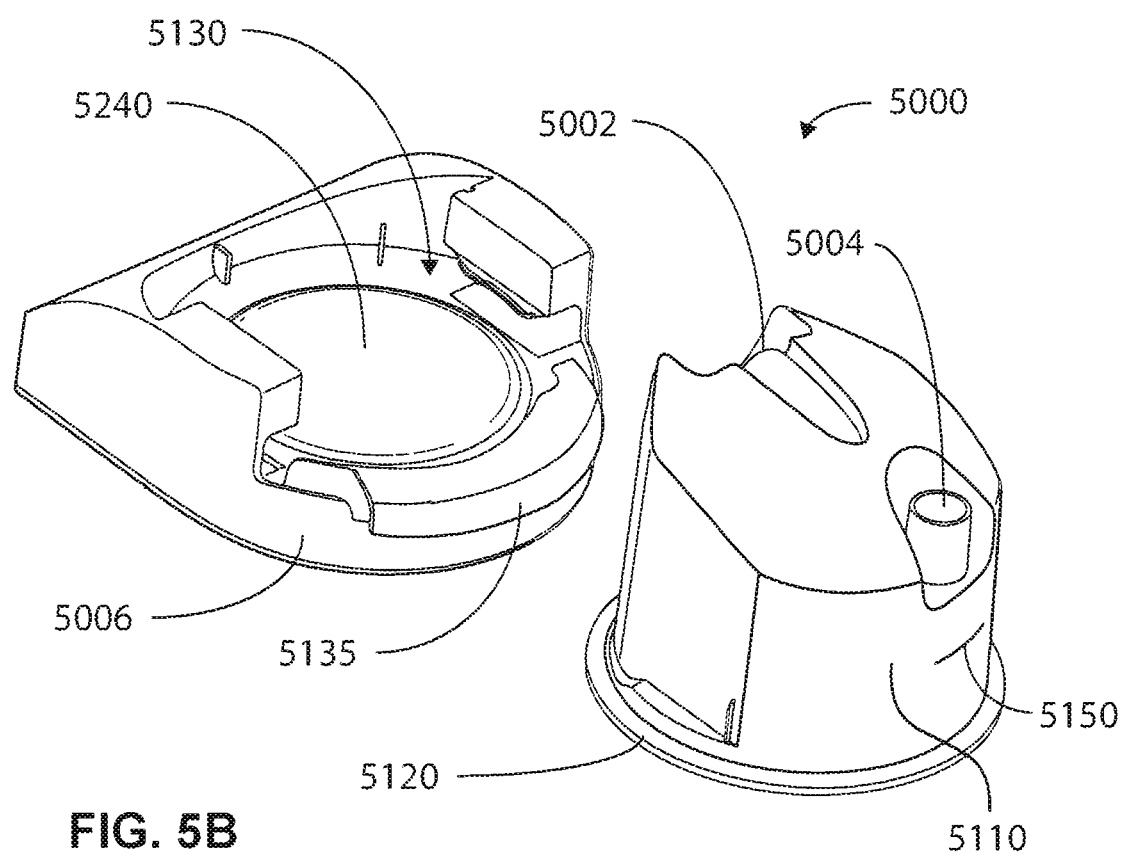

FIG. 5B shows an isometric view of a humidifier in accordance with one form of the present technology, showing a humidifier reservoir 5110 removed from the humidifier reservoir dock 5130.

4.6 Breathing Waveforms

Figure 6:
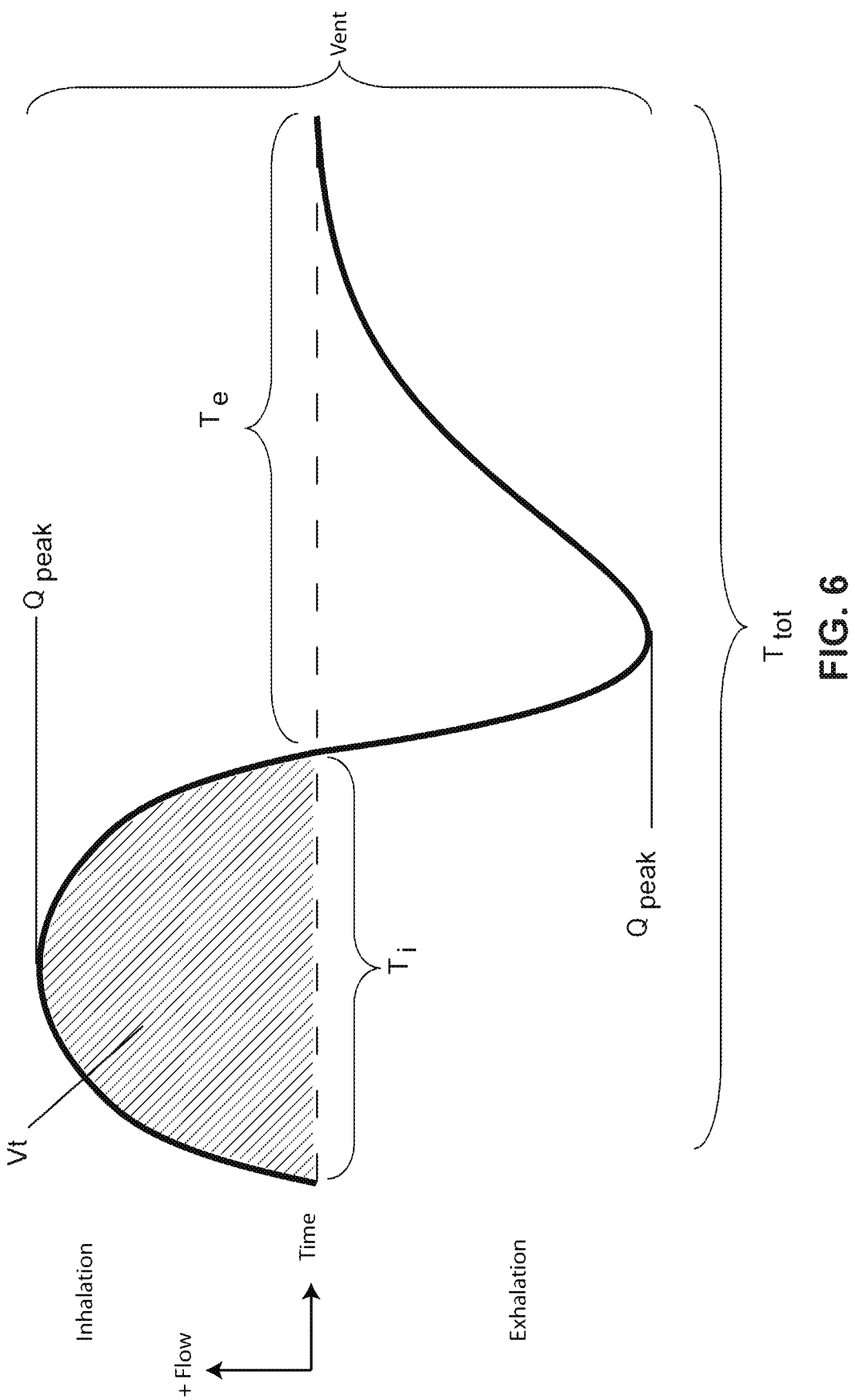

FIG. 6 shows a model typical breath waveform of a person while sleeping.

4.7 Particular Examples of the Present Technology

Figure 7:
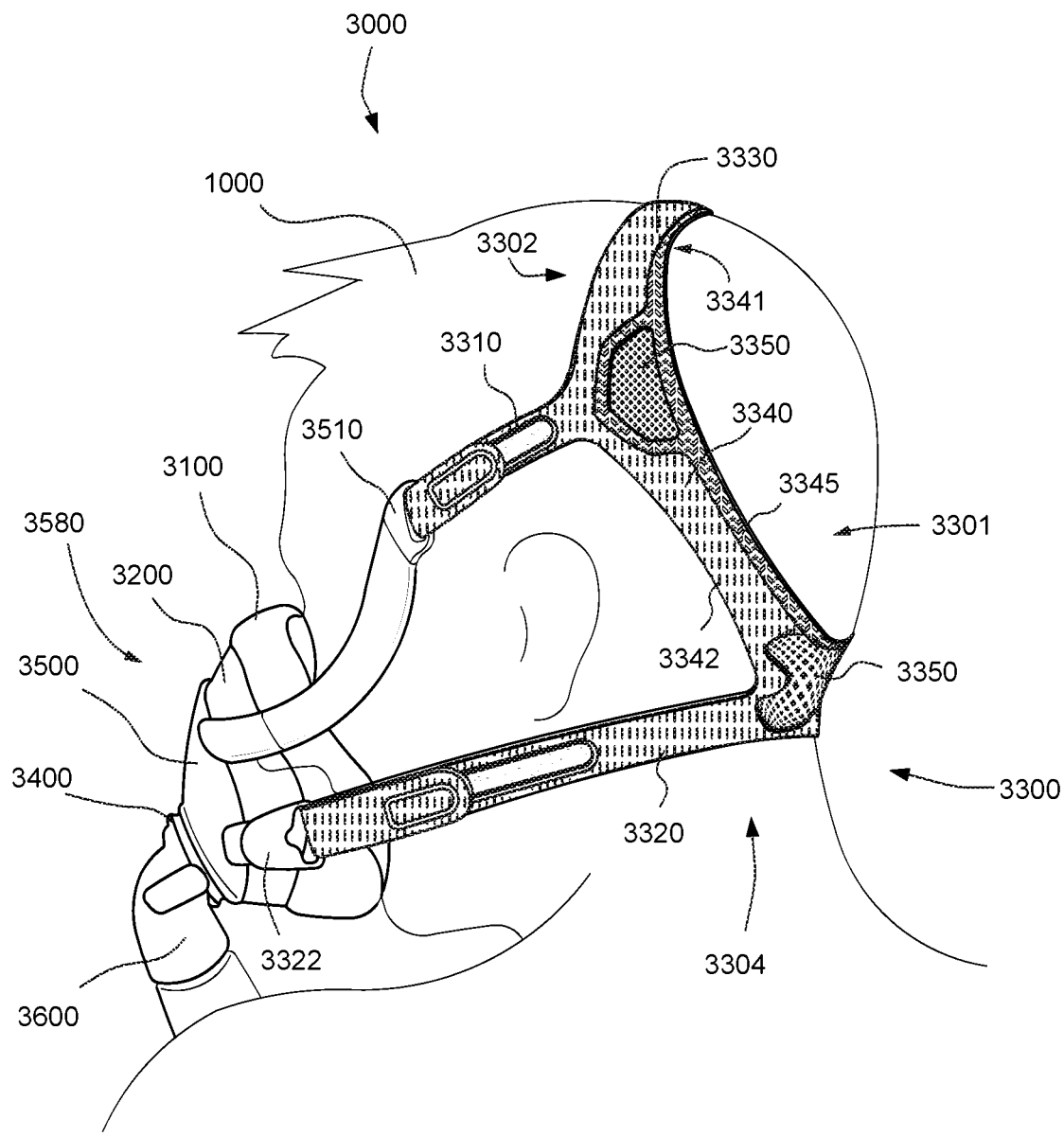

FIG. 7 shows a perspective view of a positioning and stabilising structure 3300 according to one example of the present technology, while donned by a patient 1000.

Figure 8:
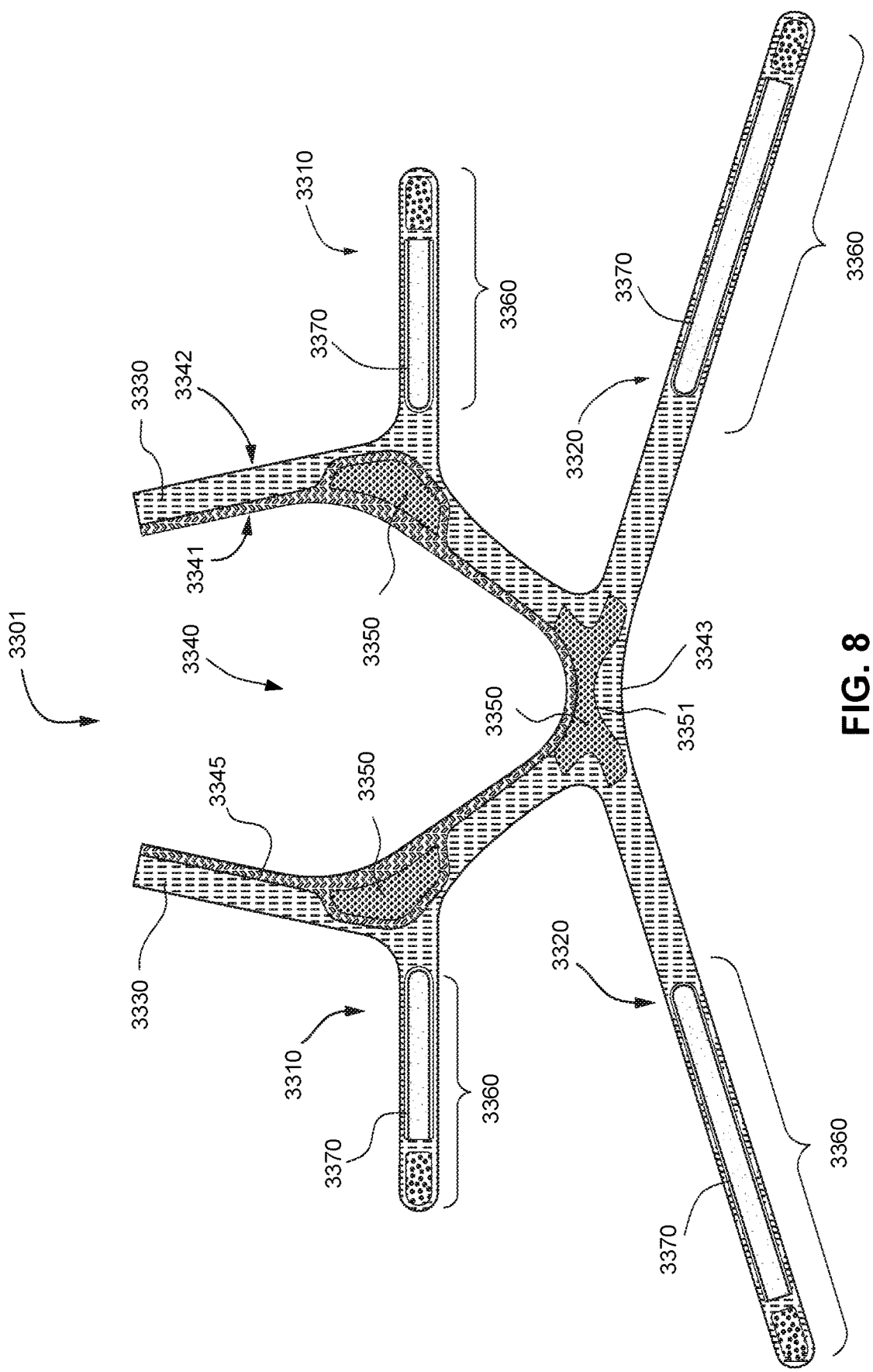

FIG. 8 shows a non-patient-contacting side view of strap portions of the positioning and stabilising structure 3300 of FIG. 7 in a flattened state.

Figure 9:
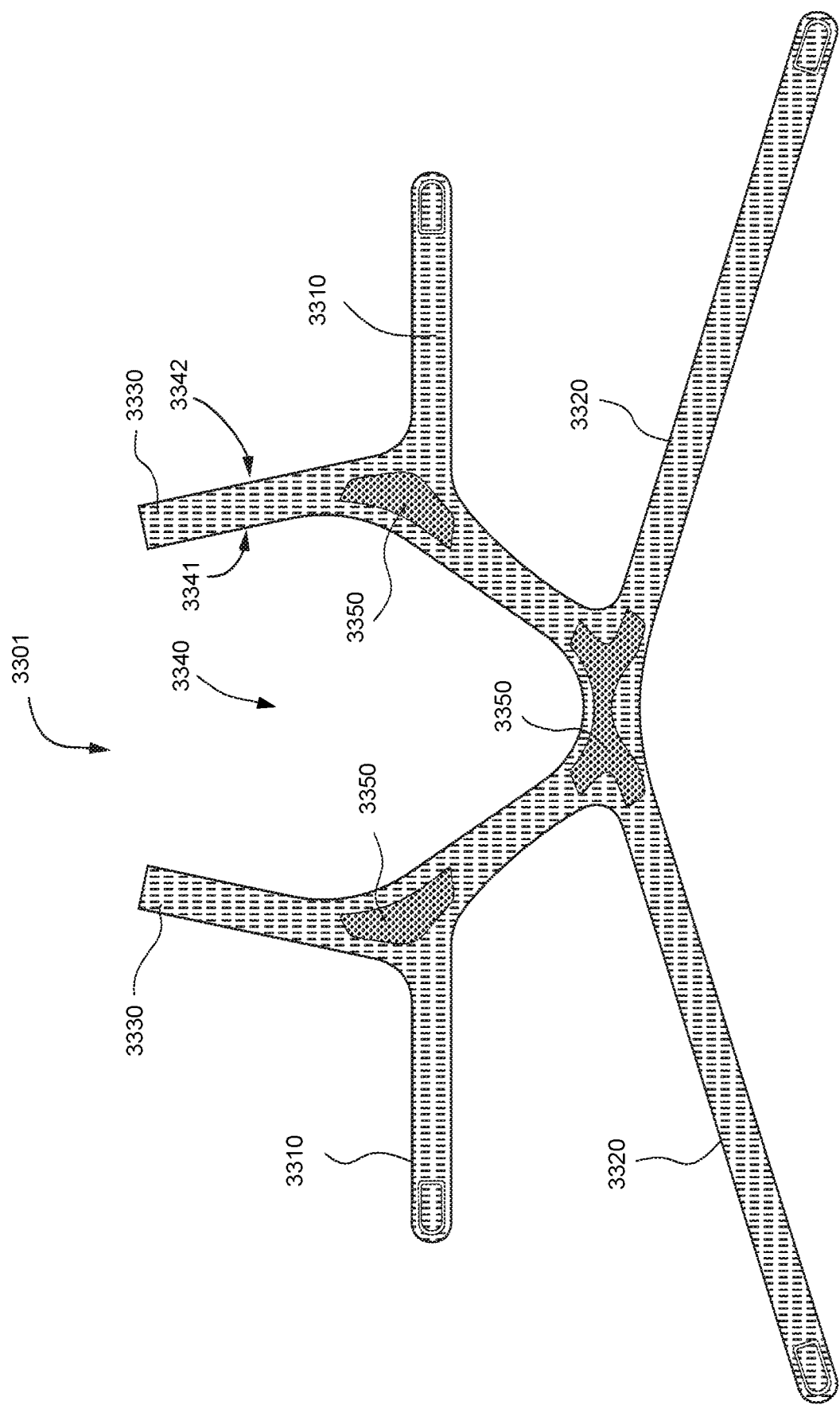

FIG. 9 shows a patient-contacting side view of strap portions of the positioning and stabilising structure 3300 of FIG. 7 in a flattened state.

Figure 10:
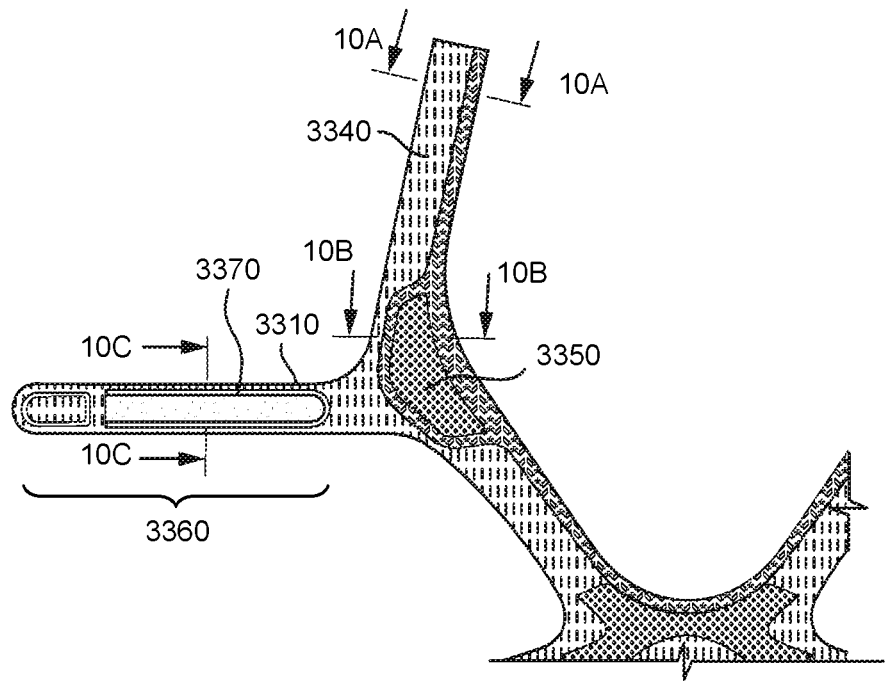
Figure 10A:
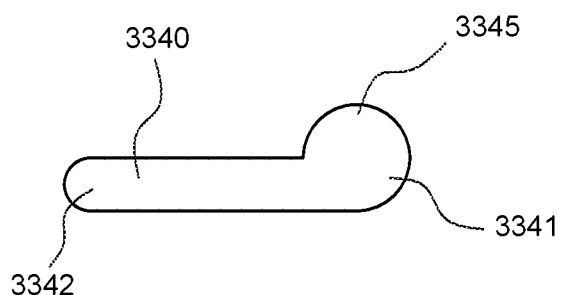
Figure 10B:
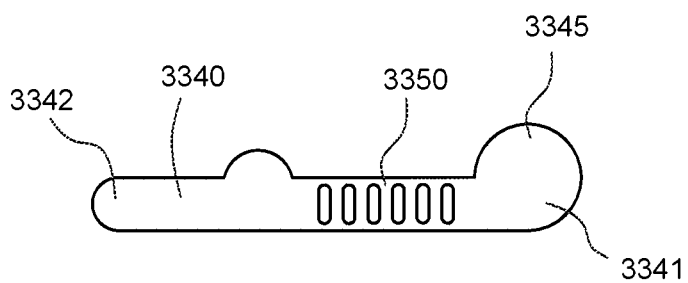
Figure 10C:
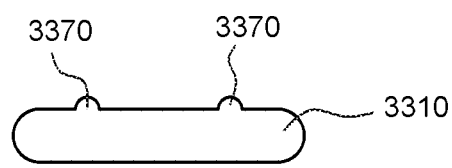

FIG. 10 shows a non-patient-contacting side view of a portion of the positioning and stabilising structure 3300 of FIG. 7 in a flattened state and with cross sections illustrated.

Figure 11:
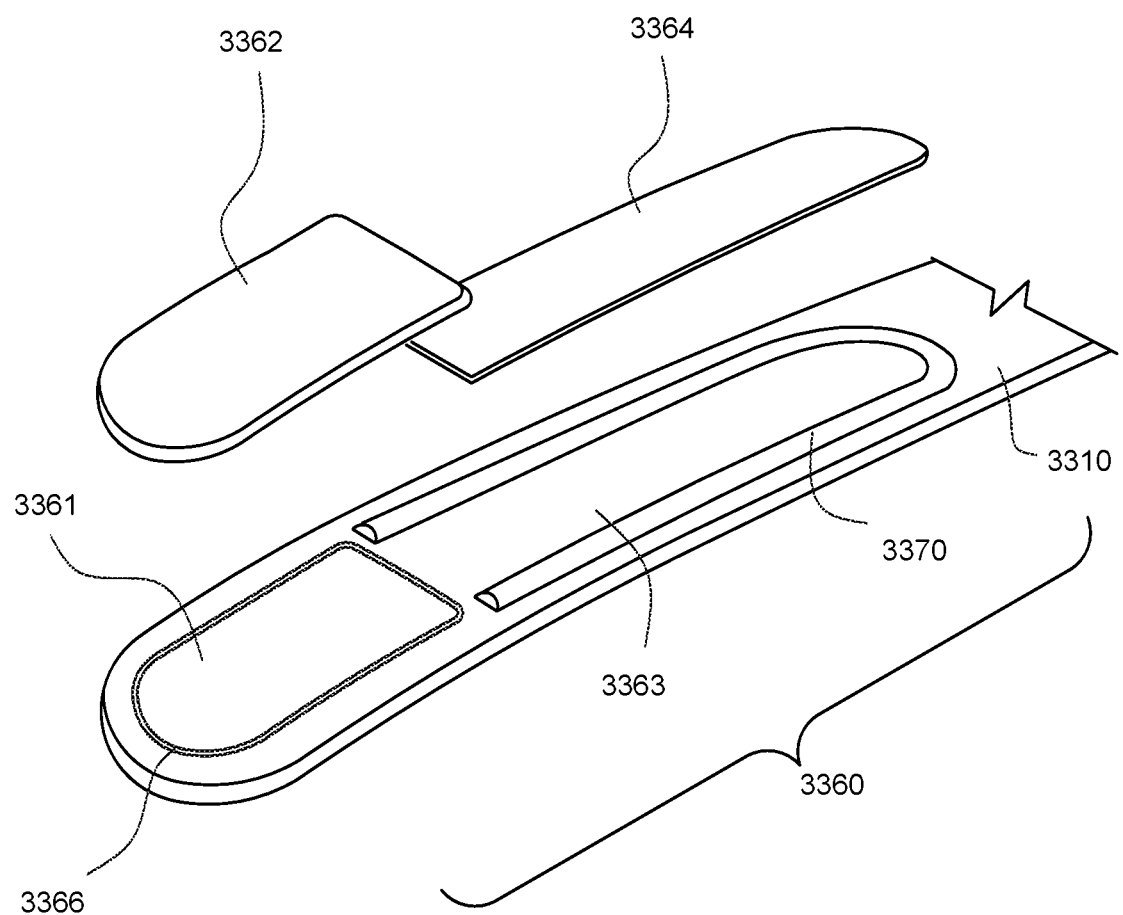

FIG. 11 shows an exploded view of a fastening portion of a strap of the positioning and stabilising structure 3300 of FIG. 7.

Figure 12:
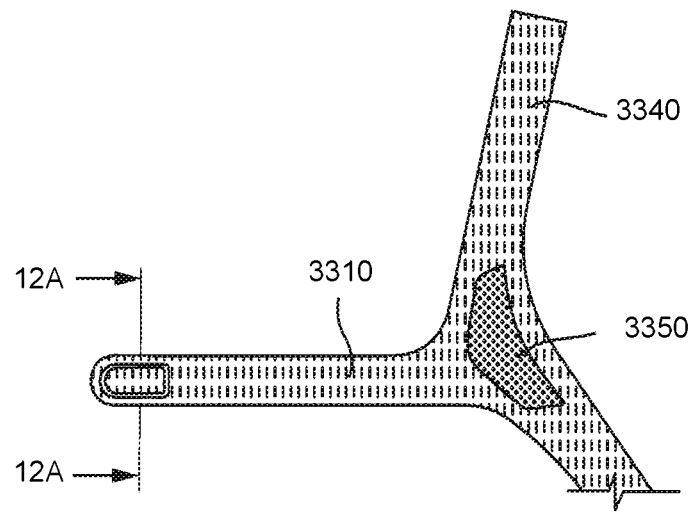
Figure 12A:
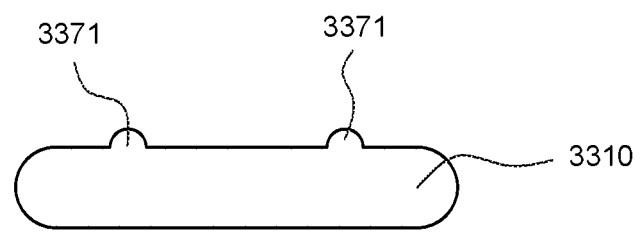

FIG. 12 shows a patient-contacting side view of a portion of the positioning and stabilising structure 3300 of FIG. 7 in a flattened state and with a cross section illustrated.

Figure 13:
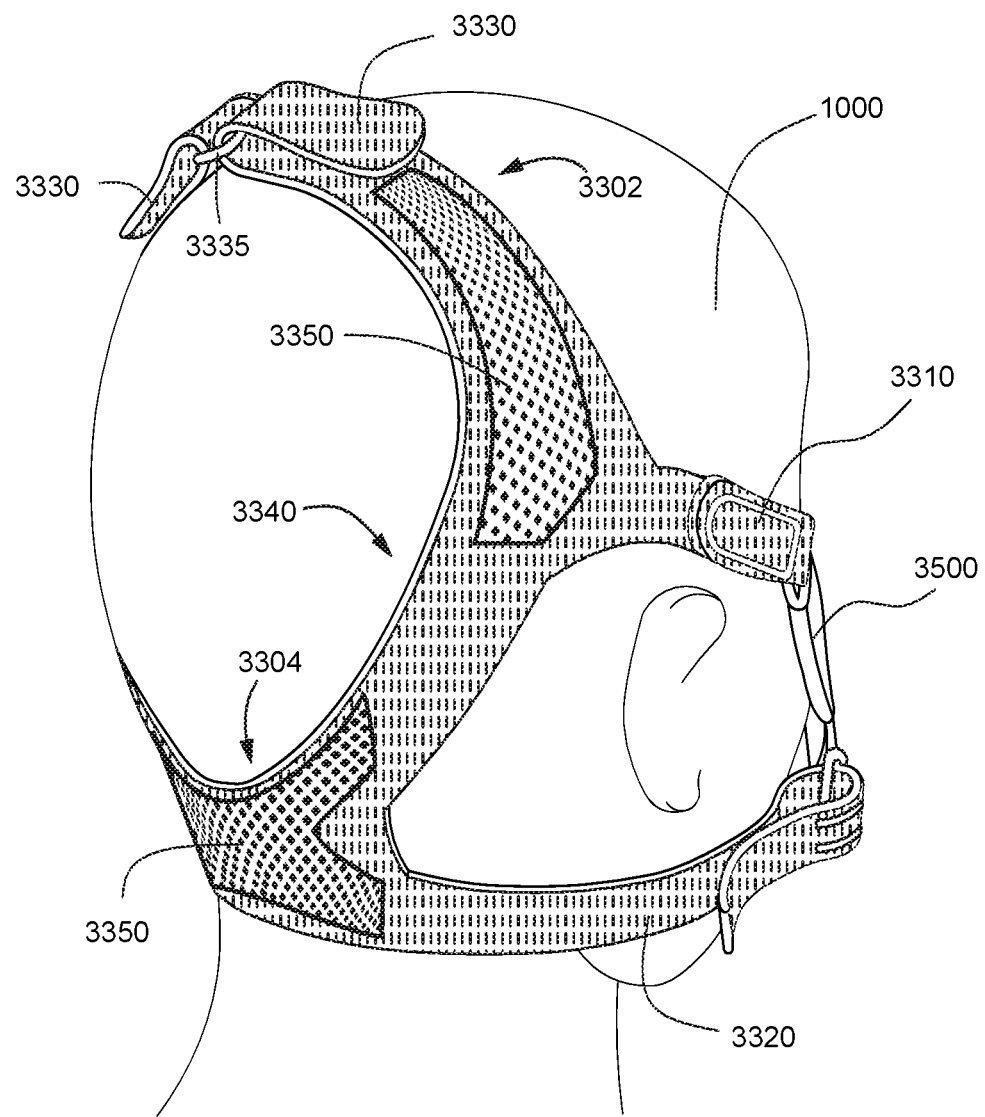

FIG. 13 shows a portion of a positioning and stabilising portion 3300 according to another example of the present technology, while donned by a patient 1000.

Figure 14:
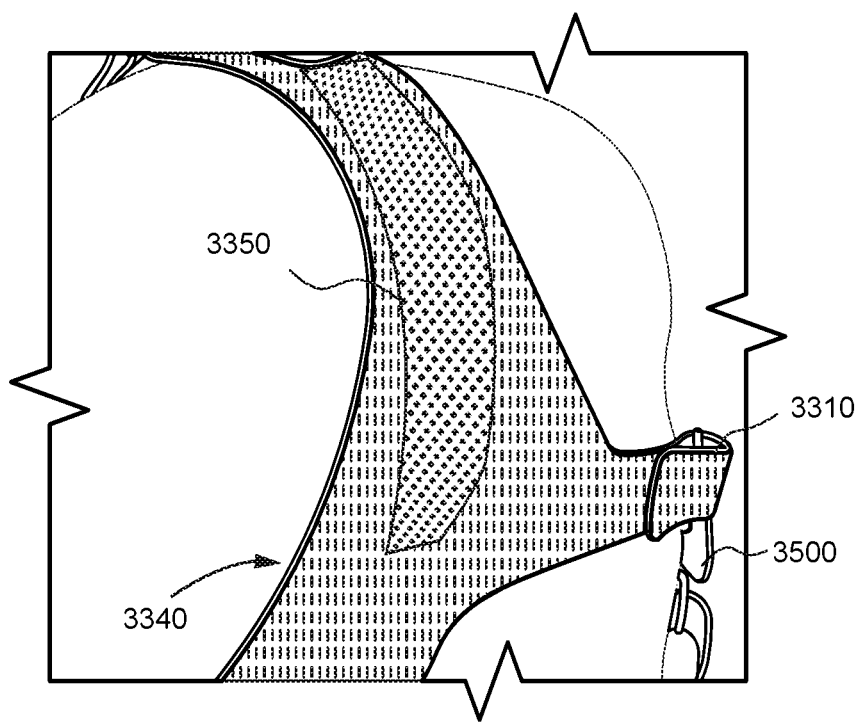

FIG. 14 shows a superior ventilation portion of the positioning and stabilising structure of FIG. 13, while donned by a patient 1000.

Figure 15:
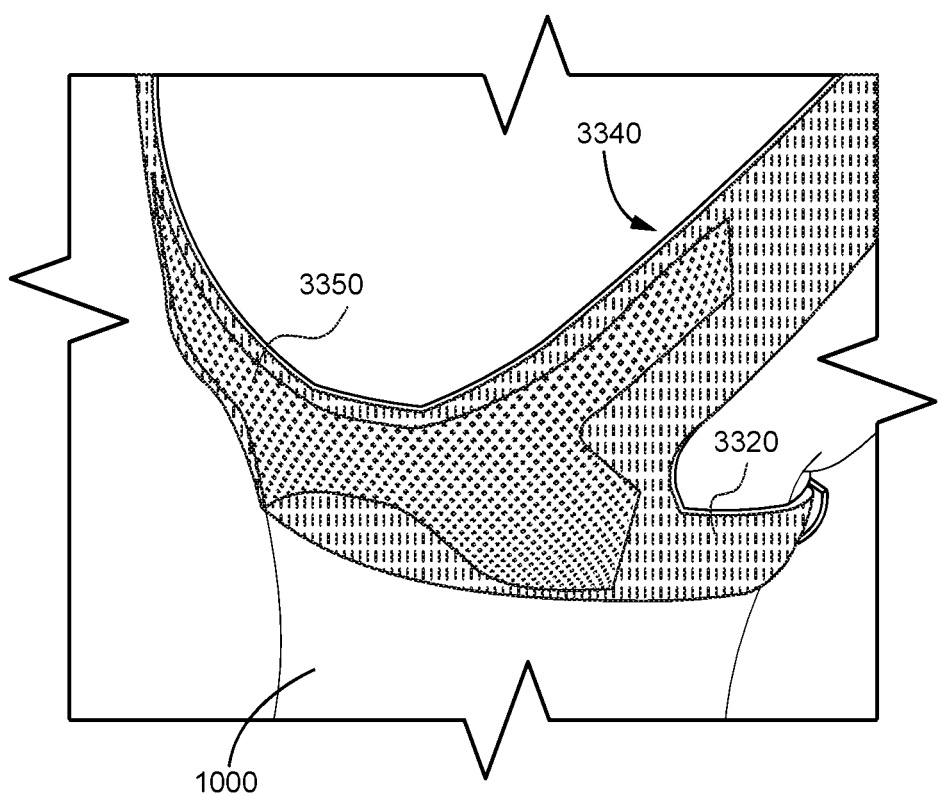

FIG. 15 shows an inferior ventilation portion of the positioning and stabilising structure of FIG. 13 while donned by a patient 1000.

Figure 16:
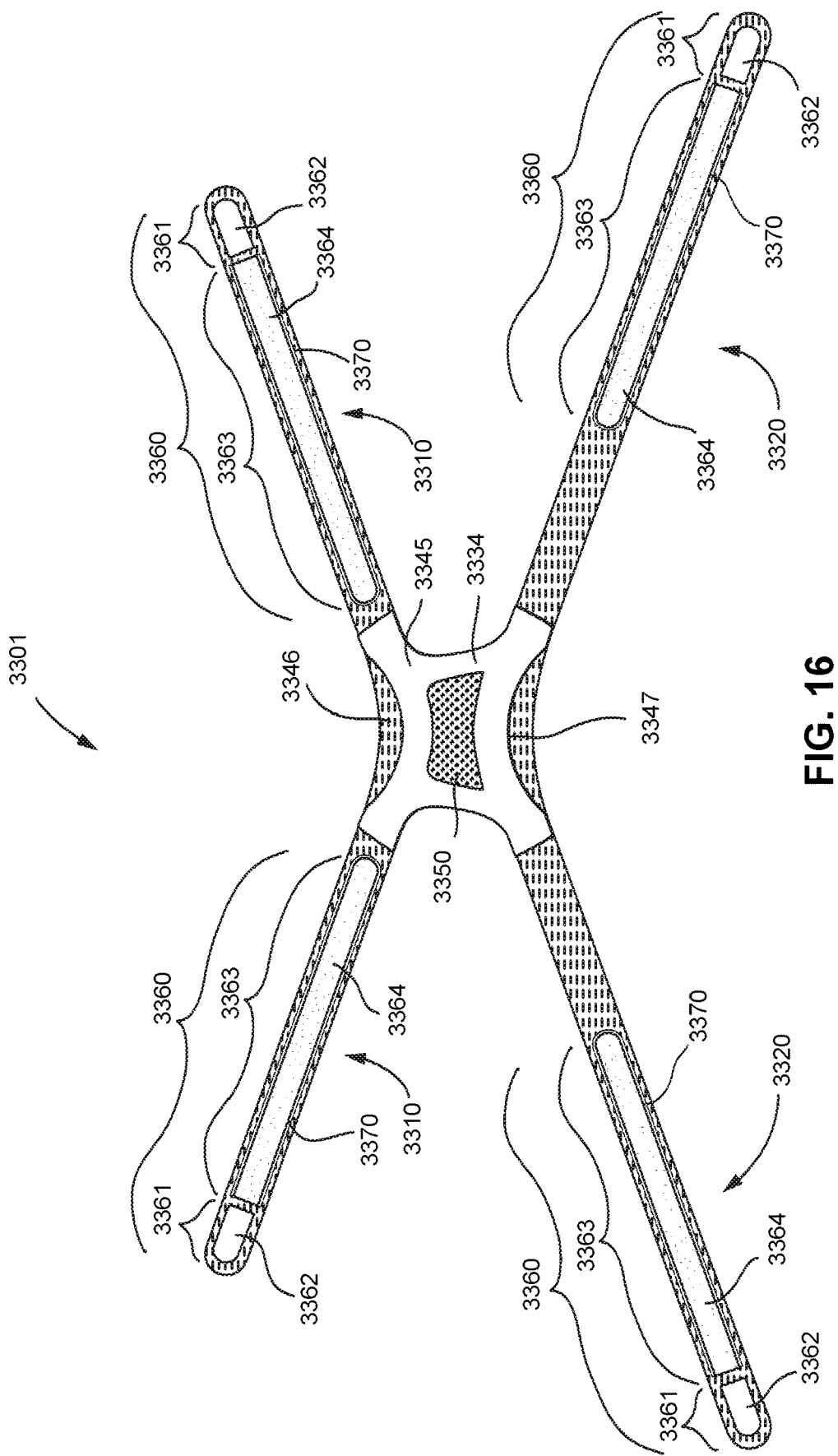

FIG. 16 shows a non-patient-contacting side view of a headgear strap 3301 of a positioning and stabilising structure according to another example of the present technology.

Figure 17:
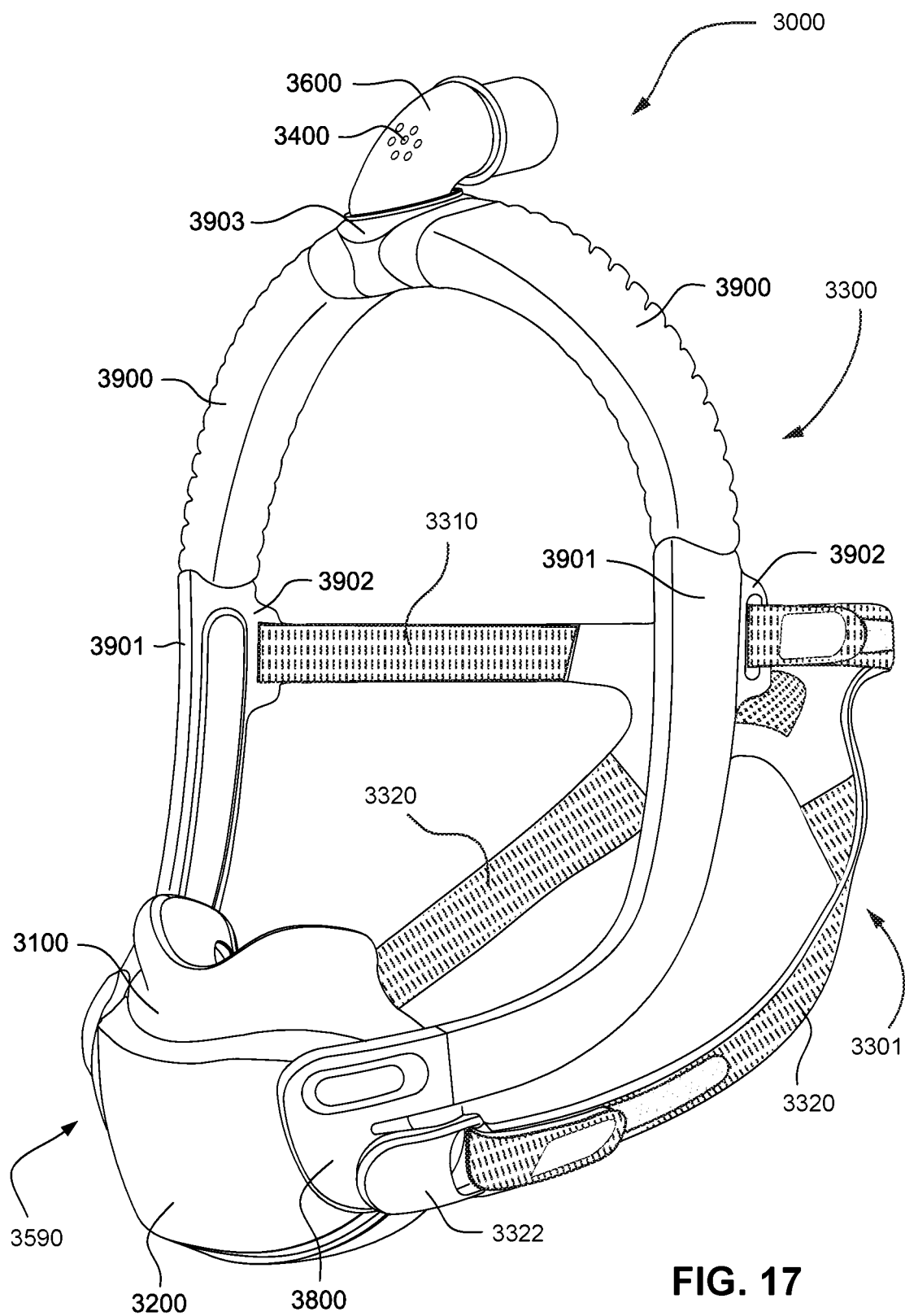

FIG. 17 shows a perspective view of a positioning and stabilising structure 3300 according to another example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 TREATMENT SYSTEMS

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent structure 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another suitable for a small sized head, but not a large sized head.

FIG. 7 shows a patient 1000 having donned a patient interface 3000 according an example of the present technology. Patient interface 3000 comprises a cushion assembly 3580 and positioning and stabilizing structure 3300. The cushion assembly may include a frame 3500, a plenum chamber 3200 connected to the frame, and a seal-forming structure 3100 provided to the plenum chamber. A cavity formed by at least the plenum chamber 3200 and seal-forming structure 3100 may be pressurisable to a therapeutic pressure of at least 6 cmH$_2$O above ambient air pressure. The plenum chamber includes a plenum chamber inlet port sized and is structured to receive a flow of air at the therapeutic pressure for breathing by the patient 1000. The patient interface 3000 in this example includes a connection port 3600, connected to an air supply conduit, which supplies air to the plenum chamber 3200.

The patient interface 3000 also comprises a seal-forming structure 3100 constructed and arranged to form a seal with a region of the patient's face surrounding an entrance to the patient's airways. The seal-forming structure 3100 has a hole therein such that the flow of air at said therapeutic pressure is delivered to at least an entrance to the patient's nares. In this example the patient interface 3000 comprises a seal-forming structure 3100 that seal around both the nose and mouth. This type of patient interface is commonly known as a full-face mask. In other examples, the seal-forming structure 3100 may seal about the patient's nares and leave the patient's mouth uncovered. The seal-forming structure 3100 is constructed and arranged to maintain said therapeutic pressure in the plenum chamber 3200 throughout the patient's respiratory cycle in use.

The patient interface 3000 further comprises a vent structure 3400. The vent structure 3400 allows a continuous flow of gases exhaled by the patient from an interior of the plenum chamber 3200 to ambient. The vent structure 3400 is sized and shaped to maintain the therapeutic pressure in the plenum chamber in use.

The patient interface 3000 also comprises a positioning and stabilising structure 3300 to provide a force to hold the seal-forming structure 3100 in a therapeutically effective position on the patient's head. The positioning and stabilising structure comprises a tie, which is constructed and arranged so that at least a portion overlies a region of the patient's head superior to an otobasion superior of the patient's head in use. In one example of the present technology, the positioning and stabilising structure 3300 comprises a frame 3500 to which the plenum chamber 3200 is connected. The frame 3500 is held in place by a number of strap portions of the positioning and stabilising structure 3300.

5.3.3.1 One-Piece Knitted Headgear Strap

In one example of the present technology, shown while donned by a patient in FIG. 7 and in isolation in FIGS. 8 and 9, the positioning and stabilising structure 3300 comprises an integrally formed headgear strap 3301. The headgear strap 3301 comprises a unitary construction. The headgear strap 3301 is formed as a single, one-piece, knitted strap, as opposed to a combination of multiple strap pieces formed separately and connected together or a one-piece strap cut from a sheet of material. Forming strap portions separately and attaching them together may be slower and/or more costly to manufacture. Cutting a headgear strap may result in significant wasted material. However, in some examples of the present technology, the positioning and stabilising structure 3300 may comprise multiple headgear strap portions that are formed separately and connected together, while including other features of the present technology that are described herein.

The headgear strap 3301 may be knitted as a single piece of material using flat knitting, directly into its final shape, without the headgear strap being cut from a sheet of material and without additional threads used to stitch individual headgear pieces together. By flat knitting the headgear strap 3301, the entire headgear strap 3301 can be knitted in a single flat knitting process. In some examples of the present technology, the headgear strap 3301 does not comprise seams or joints. Seams and joints may create uncomfortable pressure on the skin of some users in some circumstances.

One advantage of flat knitting is that the headgear strap 3301 can be knitted into the final shape directly from fibres in the form of thread, yarn or the like, rather than cut from a sheet. Cutting a plurality of complex shapes from a sheet may leave large offcuts which become waste. Furthermore, when headgear straps are cut from laminated sheets, there may be less flexibility to cost-effectively customise the headgear fabric or colour. New sheets may need to be laminated in order to create new fabric and/or colour options.

Another advantage of the knitted headgear strap 3301 is that the headgear can be knitted to conform very closely to the shape of the patient's head, enhancing comfort and stability. In some examples of the present technology, the headgear strap 3301 may be knitted to conform to the shape of a particular patient's head based on a three-dimensional model of the particular patient's head created with imaging or scanning of the particular patient's head.

Some existing headgear has been produced by double needle crochet knitting. Headgear straps produced by this method may be limited to single, strap-like profiles, rather than complete headgear for a nasal mask or a full-face mask (e.g. patient interfaces having a four-point headgear connection), due to the complex shape of four-point connection headgear straps.

In some examples of the present technology, the headgear strap 3301 is formed using sophisticated knitting techniques to form knitting structures with very good ventilation, elasticity and/or aesthetic appeal. Such knitting structures may be similar to those found in a sports jerseys.

In some examples of the present technology the headgear strap 3301 comprises a plurality of different colours and/or patterns. Flat knitting can be used to mix colours and patterns to provide a wide range of design variety without additional cosmetic cost.

In some examples of the present technology, the headgear strap 3301 comprises one or more regions of localised rigidity and/or elasticity. The regions of localised rigidity and/or elasticity may be formed in the headgear strap 3301 by a flat knitting process performed during knitting of the overall headgear strap 3301. Elastic properties can be tailored to meet the different requirements of each region of the headgear strap 3301.

In some examples of the present technology, the headgear strap 3301 is formed by flat knitting but comprises a non-flat shape even before being donned by a patient. The non-flat shape may be produced by knitting the headgear strap 3301 with different knitting densities in different regions. Different properties may be provided to different regions of the headgear strap 3301 to meet predetermined specifications. Providing such properties to the headgear strap 3301 during flat-knitting may result in the headgear strap 3301 comprising a non-flat shape, in some examples. In some forms of the present technology, the non-flat shape may provide the headgear strap 3301 with predetermined properties, such as predetermined elasticities in particular locations and/or directions, or specific force vectors applied by the headgear strap 3301 to the plenum chamber 3200 and/or seal-forming structure 3100 in use.

In some examples of the present technology, the headgear strap 3301 is customised and tailored to a specific patient's anatomy and/or preferences. Flat knitting advantageously provides the manufacturer with flexibility in using a range of yarn, applying different design patterns, applying different colours and surface geometry features. In some examples, the headgear strap 3301 is knitted by a programmable knitting machine. A headgear strap formed by flat knitting can also be highly comfortable. If a high gauge and fine yarn texture is used, the surface finish of the strap may be smooth and present a low risk of causing facial marking.

In some examples, the headgear strap 3301 may comprise one or more text, graphics, branding, logos or the like knitted into the headgear strap 3301 during a single knitting operation performed to form the headgear strap 3301.

In alternative examples, the positioning and stabilising structure 3300 may comprise one or more headgear straps.

In some alternative examples, one or more headgear strap portions are formed by a circular knitting process.

In some examples, the headgear strap 3301 can withstand a maximum force of between 10N-100N, more preferably between 15-80N, 20-60N or 25-40N without damage. In some examples, the headgear strap 3301 may comprise one or more portions having a pique knitting structure formed with 100% nylon and may be configured to withstand a maximum load at wale of between 5-8N (in some examples between 6-7N, and a maximum load at course of between 2.5-5.5N (in some examples between 3.5N-4.5N). In some examples, the headgear strap 3301 may comprise one or more portions having a pique knitting structure formed with a combination of nylon and Spandex and may be configured to withstand a maximum load at wale of between 3-6N (in some examples between 4-5N, and a maximum load at course of between 2-4N (in some examples between 2.5-3.5N). In some examples, the headgear strap 3301 may comprise one or more portions having a single jersey knitting structure formed with a combination of nylon and Spandex and may be configured to withstand a maximum load at wale of between 2.5-5N (in some examples between 3-4N, and a maximum load at course of between 1-3N (in some examples between 1.5-2.5N).

In some examples, the headgear strap 3301 is structured to dry in only a short time after being washed or becoming wet from body moisture. The headgear strap 3301 may be highly breathable and may keep the patient's skin relatively dry. The headgear strap 3301 may be configured to cause substantially no facial marking. The headgear strap 3301 may be machine washable and hand washable.

The headgear strap 3301 shown in FIG. 8 is configured to create a four-point connection to a frame 3500 or plenum chamber 3200 of a patient interface 3000. In other examples of the technology, the headgear strap 3301 may be configured to make a two-point connection to a frame 3500 or plenum chamber 3200, for example when incorporated into a patient interface 3000 of the nasal pillows or nasal cradle type. The headgear strap 3301 may connect at either one or two points to a frame 3500 or plenum chamber 3200 of a patient interface 3000 having a full-face configuration (e.g. a configuration in which the seal-forming structure 3100 seals about an inferior periphery of the patient's nose and leaves most or all of the bridge of the patient's nose uncovered). In some examples the headgear strap 3301 may be configured as a backstrap for a positioning and stabilising structure 3300 for a conduit headgear system. In such an example, the headgear strap 3301 may overlay or lie inferior to the patient's occipital bone and connect between a pair of headgear conduit tubes that lie against the lateral sides of the patient's head.

5.3.3.2 Headgear Strap Portions

As shown in FIGS. 7-9, the positioning and stabilising structure 3300 may comprise multiple strap portions. A plurality of strap portions may be provided in a single headgear strap 3301, such as in the positioning and stabilising structure 3300 of FIGS. 7-9. The positioning and stabilising structure 3300 in this example of the present technology comprises a ring strap portion 3340. The ring strap portion 3340 encircles a posterior side of the patient's head, providing a strong anchor for other strap portions that connect to the plenum chamber 3200. The ring strap portion 3340 may also be known as a crown portion, a crown strap, a rear/posterior portion or a halo.

In this example of the present technology, the ring strap portion 3340 of the positioning and stabilising structure 3300 comprises a superior portion 3302 and an inferior portion 3304. The superior portion 3302 lies in use against the patient's head over the parietal bones of the patient's head. The inferior portion 3304 is configured to lie against the patient's head over or inferior to the occipital bone of the patient's head in use. As illustrated, the ring strap portion 3340 defines a loop.

The positioning and stabilising structure 3300 comprises a pair of upper strap portions 3310. Each of the upper strap portions 3310 is configured to connect between the ring strap portion 3340 and the plenum chamber 3200. In use, each of the upper strap portions 3310 is located alongside the patient's head, on a respective side, superior to an otobasion superior of the patient's head.

In the example shown in FIGS. 7-9, the positioning and stabilising structure 3300 also comprises a pair of lower strap portions 3320. Each of the lower strap portions 3320 is configured to connect between the ring strap portion 3340 and plenum chamber 3200. In use, each of the lower strap portions 3320 is located alongside the patient's head, on a respective side, inferior to an otobasion superior of the patient's head.

Each of the upper strap portions 3310 and the lower strap portions 3320 may connect to the plenum chamber 3200 either directly or via a frame 3500 of the cushion assembly 3580. In the example illustrated in FIG. 7, upper strap portions 3310 and lower strap portions 3320 connect to the plenum chamber 3200 via a frame 3350 to which the plenum chamber 3200 is connected.

One or more of the headgear strap portions of the positioning and stabilising structure 3330 (e.g. the upper strap portions 3310, lower strap portions 3320 and the overhead strap portions 3330 described below) may comprise a fastening portion 3360. The fastening portion 3360 may be structured and/or arranged to allow the strap to be looped back and fastened onto itself. In one example, the fastening portion 3360 may comprise hook-and-loop material. In another example, the fastening portion 3360 may comprise magnets configured to be attracted to each other when the strap is looped back onto itself.

In some examples of the technology the positioning and stabilising structure 3300 may comprise upper strap portions 3310 but may not comprise lower strap portions 3320. In some examples of the present technology, a patient interface 3000 may comprise a positioning and stabilising structure 3300 comprising upper strap portions 3310 connecting a rear portion of the positioning and stabilising structure 3300, such as a ring strap portion 3340, to a plenum chamber 3200 comprising nasal pillows or a cradle cushion seal-forming structure 3100.

In this example, the ring strap portion 3340 comprises a rigidised portion 3345. The rigidised portion 3345 comprises a higher rigidity in comparison to other portions of the ring strap portion 3340. The rigidised portion 3345 may not be completely rigid but may instead be "rigidised" in the sense that it is more rigid than some or all of the other parts of the ring strap portion 3340. The rigidised portion 3345 and other portions of the ring strap portion 3340 may all be flexible to an extent, but the rigidised portion 3345 may be stiffer. The rigidised portion 3345 may be less stretchable and/or less bendable than other portions of the ring strap portion 3340. The rigidised portion 3345 is, in this example, provided along a length of the loop defined by the ring strap portion 3345. The rigidised portion 3345 of the ring strap portion 3340 may reinforce the ring strap portion 3340. Reinforcing the ring strap portion 3340 may improve the stability of the patient interface 3000 in use, since a purpose of the ring strap portion 3340 is to provide an anchor for the other strap portions which connect to the plenum chamber 3200 while under tension to pull the plenum chamber 3200 into the patient's face. The rigidised portion 3345 may be substantially non-stretchable, although may still be bendable to conform to the curvature of the patient's head. The non-stretchable nature of the rigidised portion 3345 provides reinforcement to the ring strap portion 3340, providing a firmer anchor and resulting in a more stable positioning and stabilising structure 3300. The upper strap portions 3310 may be stretchable. In some examples of the present technology, the rigidised portion 3345 may be stretchable, but less so than other portions of the ring strap portion 3340. In some examples, the ring strap portion 3340 may comprise a first portion provided along a length of the loop defined by the ring strap portion 3340 and a second portion provided along the length of the loop. The second portion may comprise the rigidised portion 3345 and may extend along an edge of the ring strap portion 3340 directly adjacent (e.g., bordering) the first portion. The second portion may comprise a greater stiffness than the first portion. The second portion may be less bendable than the first portion. The second portion may be less stretchable than the first portion.

In this example of the technology, the rigidised portion 3345 is provided along substantially the entire length of the loop defined by the ring strap portion 3340. As illustrated, the ring strap portion 3340 comprises an inside periphery (or inner edge) 3341 and an outside periphery (or outer edge) 3342. In some examples, the ring strap portion 3340 is stiffer at or proximate the inside periphery 3341 than at or proximate the outside periphery 3342. In one example, the rigidised portion 3345 is provided to the ring strap portion 3340 proximate the inside periphery 3341 (e.g., along an inner edge) of the ring strap portion 3340. The rigidised portion 3345 may define the inside periphery 3341 (or inner edge) of the ring strap portion 3340 or, alternatively, may be located close to an edge of the ring strap portion 3340 defining the inside periphery 3341. The rigidised portion 3345 may form substantially the entire inside periphery 3341 of the ring strap portion 3340. In other examples, the rigidised portion 3345 may be provided substantially centrally between the inside periphery 3341 of the ring strap portion 3340 and the outside periphery 3342 of the ring strap portion 3340.

Reinforcing the inside periphery 3341 around the ring strap portion 3340 may be advantageous because the outside periphery 3342 (the more anterior side) of the ring strap portion 3340 may then be able to be formed contiguously with any other strap portions connecting the ring strap portion 3340 with the plenum chamber 3200 of the patient interface 3000. Positioning the rigidised portion 3345 centrally between the inside periphery 3341 and the outside periphery 3342 may have an advantage in even distribution of pressure loading on the patient's skin. The inside periphery 3341 of the ring strap portion 3340 may also not need to deform as much as the outside periphery 3342 since it is the outside periphery 3342 from which further strap portions extend to connect to the plenum chamber 3200 in front of the patient's face.

The ring strap portion 3340 and/or any other strap portions of the positioning and stabilising structure 3300 may comprise rounded edges. A rounded edge may be less likely to cause skin marking and may be more comfortable on the patient's skin.

In some examples of the present technology, the strap portions of the positioning and stabilising structure 3300 may be formed by knitting. That is, one or more of the upper strap portions 3310, lower strap portions 3320 and the ring strap portion 3340 may comprise a knitted fabric structure. In some examples, one or more of these strap portions of the positioning and stabilising structure 3300 may be formed by flat knitting. For example, the ring strap portion 3340, upper strap portions 3310 and/or lower strap portions 3320 may comprise a single jersey knitted structure and may be formed from a combination of nylon and spandex. A single jersey knitted structure advantageously provides the necessary flexibility and elasticity for the strap portions without excessive thickness. Alternatively, the ring strap portion 3340 may comprise a double jersey loop formation. The rigidised portion 3345 of the ring strap portion 3340 may comprise a pique knitting structure (e.g., a pique rib structure) and may be formed from nylon or a combination of nylon and spandex. It may be advantageous to use a pique knitting structure to form the rigidised portion 3345 since this type of structure is well-suited to create a ridge having a sufficiently high level of rigidity while also having a rounded edge. That is, the first portion of the ring strap portion 3340 and the second portion (e.g., the rigidized portion 3345) of the ring strap portion may comprise the same type yarn (e.g., yarn having the same stiffness), whereas the second portion may have increased rigidity as compared to the first portion due to the different knit structure. In an example, the pique knit structure may provide increased rigidity as compared to the knit structure (e.g., single or double jersey knit) of the first portion of the ring strap portion.

The headgear straps of the positioning and stabilising structure 3300 may be stretchable. Advantageously, the upper strap portions 3310, lower strap portions 3320 and ring strap portion 3340 are stretchable. The stretchable nature of the ring strap portion 3340 of the positioning and stabilising structure 3300 enables the ring strap portion 3340 to conform and fit snugly to the posterior, lateral and superior surfaces of the patient's head in use. Stretchiness in the upper strap portions 3310 and lower strap portions 3320 enables these strap portions to extend in length slightly to provide some relief when the plenum chamber 3200 is pressurised. When the plenum chamber 3200 is under pressure in use, the volume of pressurised air inside the plenum chamber 3200 pushes the plenum chamber 3200 and frame 3500 in an anterior direction away from the patient's face. The force from this pressure must be countered by tension in the headgear straps in order to keep the plenum chamber 3200 and seal-forming structure 3100 in sealed contact with the patient's face. The ability of the upper strap portions 3310 and lower strap portion 3320 to extend in length by at least a small amount can make wearing the patient interface 3000 more comfortable when this occurs.

Advantageously, the upper strap portions 3310, lower strap portions 3320 and ring strap portion 3340 are all breathable due to the knitted structure with which they are formed. Breathability is advantageous as it can keep the headgear straps and the patient's skin dry while keeping the temperature of the patient's skin underneath the headgear straps manageable.

The rigidised portion 3345 may be a round, thickened portion of headgear strap material. The rigidised portion 3345 may comprise an increased material thickness relative to adjacent portions of the ring strap portion 3340. In some examples of the present technology a patient-contacting side of the ring strap portion 3340 is substantially flat and the increased material thickness is provided to a non-patient-contacting side of the ring strap portions 3340. Advantageously, achieving extra thickness by providing the extra material forming the rigidised portion 3345 on the non-patient-contacting side of the ring strap portion 3340 keeps the patient-contacting side of the ring strap portion 3340 substantially flat. A flat surface may advantageously be more comfortable against a patient's skin than a non-flat surface. Since, in the example shown in FIG. 7, the rigidised portion 3345 is provided to the inside periphery 3341 of the ring strap portion 3340, the inside periphery 3341 is thicker than the outside periphery 3342. In use, a posterior edge of the ring strap portion 3340 is thicker than anterior edges of the ring strap portion 3340. A thicker inside periphery 3341 in comparison to the outside periphery 3342 results in a stiffer inside edge of the ring strap portion 3340, providing reinforcement to the ring strap portion 3340.

The reinforcement of the reinforced portion 3345 may not be discernible on the patient-contacting side of the ring strap portion 3340. In use, the patient may not be able to see and/or feel any features of the reinforced portion 3345. In FIG. 10, the cross section at two locations of the ring strap portion 3340 is illustrated. As illustrated, extra thickness at the rigidised portion 3345 is provided to only one side of the ring strap portion 3340 (the non-patient-contacting side). The other side of the ring strap portion 3340 is substantially flat. Additionally, the rigidised portion 3345 is rounded, as is the inside edge of the ring strap portion 3340 (at the inside periphery 3341) and the outside edge of the ring strap portion 3340 (at the outside periphery 3342). Smooth/rounded edges may apply only a light pressure on the uses face, which may be particularly useful for maintaining comfort even if the patient overtightens the headgear straps.

In some examples of the present technology, the ring strap portion 3340 comprises a thickness in the rigidised portion 3345 within the range of 3-5 mm, such as within the range of 3.5-4.5 mm. The rigidised portion 3345 may comprise a thickness of 4 mm in some examples. The ring strap portion 3340 may comprise a thickness within the range of 1.5-3.5 mm, such as within the range of 2-3 mm, for example 2 mm, at regions of the ring strap portion 3340 other than the rigidised portion 3345. The upper strap portions 3310 and lower strap portions 3320 may also comprise a thickness within the range of 1.5-3.5 mm, such as within the range of 2-3 mm, for example 2 mm.

The rigidity of the rigidised portion 3345 may, in some examples, not be uniform along the length of the ring strap portion 3340. The rigidised portion 3345 may be less stretchable and/or flexible in some locations in comparison to other locations around the ring strap portion 3340. In some examples, the rigidised portion 3345 may be larger in particular locations (in comparison to other locations) such that it has an increased rigidity and/or stiffness at those particular locations. As illustrated in FIGS. 7-8, the rigidised portion 3345 is larger proximate the junctions of the upper strap portions 3310 and the ring strap portion 3340. In this example the rigidised portion 3345 is wider proximate the upper strap portions 3310 than at other locations along the ring strap portion 3340. In other examples of the present technology, the rigidised portion 3345 may be more rigid at particular locations due to an increased material thickness and/or the use of a different knitting structure (in examples in which the ring strap portion 3340 is formed by knitting).

The width and/or material thickness may vary along the length of the ring strap portion 3340 to provide stiffness in locations where stiffness/stability is required and to provide for flexibility and/or comfort where stiffness is less required. Extra stiffness may be particularly advantageous proximate the junction of the upper strap portions 3310 and the ring strap portion 3340 since, in use, the upper strap portions 3310 are under tension and there is a relatively large area of the strap material at the junction. Strengthening this junction may help provide a high level of stability to the patient interface 3000.

The superior portion 3302 of the ring strap portion 3340 may comprise one or more overhead strap portions 3330. As shown in FIGS. 8, 9 and 13, in one example the ring strap portion 3340 comprises a pair of overhead strap portions 3330. The overhead strap portions 3330 may be configured to adjust the connection to each other. In one example, the overhead strap portions 3330 are configured to adjustably connect to each other proximate the sagittal plane of the patient's head. An adjustable connection between the two overhead strap portions 3330 may advantageously enable the positioning and stabilising structure 3300 to fit to a range of patient head shapes and sizes. In other examples of the present technology, the positioning and stabilising structure 3330 may comprise a single overhead strap portion 3330. If only a single overhead strap portion 3330 is provided, it may be elastically extendable in length to fit a range of patient head sizes.

The two overhead strap portions 3330 may be adjustably connected together with a buckle 3335. The buckle 3335 may comprise a pair of slots, eyelet or other openings through which the overhead strap portions 3330 can pass, enabling each overhead strap portion 3330 to be passed through a portion of the buckle 3335 and secured back onto itself. The overhead strap portions 3330 may each comprise hook-and-loop fastening material enabling the end portion of each overhead strap portion 3330 to be fastened to an intermediate portion of the respective overhead strap portion 3330. In other examples of the present technology, each overhead strap portions 3330 may be fastened back onto itself with a clip, elastic band, magnet or other suitable fastening means. In alternative examples, two overhead strap portions are formed separately during manufacturing of the positioning and stabilising structure 3300 and then welded or sewn together to complete the loop formed by the ring strap portion 3340.

FIG. 16 shows a headgear strap 3301 of a positioning and stabilising structure 3300 according to another example of the present technology. This headgear strap 3301 may be integrally formed by knitting and may be formed in a single flat knitting process as a single piece of material. The headgear strap 3301 of FIG. 16 may include any of the features and/or properties of the headgear straps 3301 described with reference to FIGS. 7-15.

The headgear strap 3301 shown in FIG. 16 comprises a pair of upper headgear strap portions 3310, each configured to connect to a plenum chamber 3200 of a patient interface 3000 in use. In this example, each of the upper headgear strap portions 3310 is configured to connect to a respective headgear conduit of the positioning and stabilising structure 3330 located on a respective lateral side of the patient's head in use. The headgear conduits may be each be configured to extend from a medial location on a superior portion of the patient's head laterally across the superior portion of the patient's head, inferiorly at the lateral sides of the patient's head and then anteriorly and medially to connect to the plenum chamber 3200 proximate an entrance to the patient's airways. Accordingly, the upper headgear strap portions 3310 are configured to connect to the plenum chamber 3200 via headgear conduits. The headgear strap 3301 also comprises a pair of lower headgear strap portions 3320, each configured to connect to the plenum chamber 3200. The lower headgear strap portions 3320 may connect directly to the plenum chamber 3200 or a frame 3500 of the cushion assembly 3580.

FIG. 17 shows a patient interface 3000 comprising a cushion assembly 3590 and a positioning and stabilising structure 3300, according to another example of the present technology. The cushion assembly 3590 includes the plenum chamber 3200 and the seal-forming structure 3100. The positioning and stabilising structure 3300 includes a headgear strap 3301, configured for use with the conduit headgear of the patient interface. The headgear strap 3301 shown in FIG. 17 connects to headgear conduits 3900 in the same manner as the headgear strap shown in FIG. 16. As illustrated, the headgear conduits are joined at a junction 3903 at a superior portion of the patient's head. A connection port 3600 supplies a pressurised flow of breathable gas to the headgear conduits 3900. Each headgear conduit 3900 comprises a lateral portion 3901 alongside the patient's head which connects to a plenum chamber 3200 located at an entrance to the patient's airways in use via a connector 3800. More generally, each headgear conduit 3900 may receive the flow of air from a connection port 3600 on top of the patient's head and deliver the flow of air to the entrance of the patient's airways via the seal-forming structure 3100, each headgear conduit 3900 constructed and arranged to contact, in use, at least a region of the patient's head superior to an otobasion superior of the patient's head on a respective side of the patient's head.

As shown in FIG. 17, the positioning and stabilising structure 3300 comprises a pair of upper strap portions 3310 which connect between a neck strap portion 3334 and respective headgear conduits 3900. The neck strap portion 3334 may also be referred to as a rear/posterior portion. In this example the upper strap portions connect to eyelets on tabs 3902 of the headgear conduits 3900. The lower strap portions 3320 connect between the neck strap portion 3334 and the plenum chamber 3200, in this example via headgear clips 3322.

In the examples shown in FIGS. 16 and 17, the headgear strap 3301 does not comprise a ring strap portion or overhead strap portions since, in the positioning and stabilising structure 3300 for which the headgear strap 3301 is configured, the headgear conduits provide the functions of the ring strap portion and overhead strap portions of the examples shown in FIGS. 7-15. However, some examples of the present technology include a positioning and stabilising structure 3300 comprising headgear conduits as well as a headgear strap 3301 comprising a ring strap portion 3340 and/or overhead strap portions 3330.

The headgear strap 3301 shown in FIGS. 16 and 17 comprises a neck strap portion 3334. The neck strap portion 3334 connects each of the upper headgear straps 3310 and lower headgear straps 3320. The neck strap portion 3334 is configured to lie against a posterior surface of the patient's neck in use and/or a surface of the patient's head overlying an occipital bone of the patient's skull. The neck strap portion 3334 may be configured to overlay the occipital bone of the patient's head and/or lie against the patient's neck in use.

The neck strap portion 3334, upper headgear strap portions 3310 and lower headgear strap portions 3320 may be integrally formed. The headgear strap 3301 and its upper headgear strap portions 3310, lower headgear strap portions 3320 and neck strap portion 3334 may be formed by a single flat knitting process.

The headgear strap 3301 shown in FIG. 16 comprises a rigidised portion 3345. In this example the rigidised portion 3345 is provided to the neck strap portion 3334. The rigidised portion 3345 may be formed in any of the same ways as described above in relation to the rigidised portion 3345 of the positioning and stabilising structures 3300 shown in FIGS. 7-15, such as with an increased thickness and/or more rigid knitting structure. The rigidised portion 3345 in this example may be substantially non-stretchable.

The rigidised portion 3345 may reinforce the neck strap portion 3334. This reinforcement may provide a high level of stability to the patient interface 3000 in use, since a purpose of the neck strap portion 3334 is to provide an anchor for the other strap portions which connect to the plenum chamber 3200 while under tension to pull the plenum chamber 3200 towards the patient's face. The rigidised portion 3345 may be substantially non-stretchable or at least less stretchable than the other strap portions, although may still be bendable to conform to the curvature of the patient's head. The non-stretchable or low-stretch nature of the rigidised portion 3345 provides reinforcement to the neck strap portion 3334, providing a firmer anchor and resulting in a more stable positioning and stabilising structure 3300. The upper strap portions 3310 and lower strap portions 3320 may be stretchable.

The neck strap portion 3334 may comprise stretchable portions in addition to the rigidised portion 3345. In the example shown in FIG. 16, the neck strap portion 3334 comprises stretchable portions superior and inferior to the rigidised portion 3345. The neck strap portion 3334 in this example comprises a superior stretchable portion 3346 and an inferior stretchable portion 3347. The stretchable portions may be provided to superior and/or inferior edges of the neck strap portion 3334. In this example the superior stretchable portion 3346 is provided along a superior edge of the neck strap portion 3334 and the inferior stretchable portion 3347 is provided along an inferior edge of the neck strap portion 3334. Providing stretchable portions at the superior and inferior edges of the neck strap portion 3334 may be advantageous for patient comfort. The superior and inferior edges of the neck strap portion 3334, if made to be substantially rigid, could in this configuration concentrate force from headgear tension on the patient's skin. Providing stretchable portions at the superior and inferior edges may provide some relief, improving patient comfort. The stretchable portions may also enable the neck strap portion 3334 to conform to the curvature of the patient's neck.

5.3.3.3 Headgear Ventilation

In some forms of the present technology, the positioning and stabilising structure comprises headgear straps having one or more ventilation portions structured and/or arranged to provide increased breathability through the headgear straps. As shown in FIGS. 7-10, the positioning and stabilising structure 3300 comprises three ventilation portions 3350. In this example, each of the ventilation portions 3350 are provided in the ring strap portion 3340 and each provide a region of increased breathability through the ring strap portion 3340. The ring strap portion 3340 comprises a ventilation portion 3350 proximate each of the upper strap portions 3310 (e.g. at each junction between an upper strap portion 3310 and the ring strap portion 3340). Additionally, the ring strap portion 3340 comprises a single ventilation portion 3350 proximate the junction between each of the lower strap portions 3320 and the ring strap portion 3340.

In this example, the lower strap portions 3320 both extend from the ring strap portion 3340 at a similar location. In examples of the technology in which lower strap portions 3320 extend from more distinct locations around the ring strap portion 3340, two separate ventilation portions 3350 may be provided, one at each of the junctions between a lower strap portion 3320 and the ring strap portion 3340. The ventilation portions 3350 may be provided at locations where the headgear straps comprise a relatively large area/footprint on the patient's head. These regions may be most susceptible to increases in skin temperature and/or moisture buildup. The junctions between the ring strap portion 3340 and the upper strap portions 3310 and lower strap portions 3320 may cover a relatively large surface area on the patient's skin meaning extra breathability may be desirable at these locations to provide a high level of patient comfort. The ventilation portions 3350 may advantageously prevent buildup of moisture in the headgear material and/or on the patient's skin. The ventilation portions 3350 are areas of localised breathability. The knitted structure of the other headgear strap portions of the positioning and stabilising structure 3300 may also be highly breathable, but the ventilation portions 3350 may be particularly breathable due to the meshed knitting structure used to form the ventilation portion 3350. The ventilation portions 3350 also advantageously keep the patient's skin cool, at least under the ventilation portions 3350, by facilitating fresh air exchange through the material forming the headgear strap 3301.

The ventilation portions 3350 may comprise a knitted fabric structure. The knitted fabric structure may be formed during the same knitting process that is performed to form the ring strap portion 3340, rigidised portion 3345, upper strap portions 3310 and/or lower strap portions 3320. In one example, the ventilation portions 3350 comprise a pique mesh knitting structure. The ventilation portions 3350 may be stretchable. However, in some examples the ventilation portions 3350 may be less stretchable than other headgear strap portions. A relatively low elasticity in the ventilation portions 3350 may prevent the mesh structure from being stretched to such an extent that the openings forming the mesh structure are occluded by the fabric, which could reduce breathability. The ventilation portions 3350 may be formed from nylon or from a combination of nylon and spandex, as examples.

In some examples, as shown in FIGS. 7, 8 and 10, the rigidised portion 3345 of the ring strap portion 3340 may surround the ventilation portions 3350. Advantageously, this may provide for additional stiffness at regions of the headgear strap portions that have a large surface area and may otherwise be overly flexible. That is, due to the knitting structure, the ventilation portions 3350 may provide areas of the ring strap portion 3340 that have reduced stiffness and/or increased flexibility as compared to other areas of the ring strap portion (e.g., the first portion and/or the second portion (e.g., rigidized portion 3345) of the ring strap portion). The rigidized portions 3345 may be provided adjacent (e.g., directly adjacent, e.g., bordering) the ventilation portions 3350 to provide increased rigidity next to or surrounding the ventilation areas. Not every ventilation portion 3350 may be surrounded by rigidised portion 3345. In the example shown in FIGS. 7, 8 and 10, the ventilation portion 3350 proximate the patient's neck is not surrounded by a rigidised portion 3345. However, the ventilation portions 3350 proximate the upper strap portions 3310 surrounded by the rigidised portion 3345.

The ring strap portion 3340 comprises a pair of superior ventilation portions 3350, each being provided proximate a respective upper strap portion 3310. As described above, the rigidised portion 3345 surrounds each of the superior ventilation portions 3350. In this example, the rigidised portion 3345 comprises a higher material thickness on a posterior side of each of the superior ventilation portions 3350 than on an anterior side of each of the superior ventilation portions

3350. As described above, the rigidised portion 3345 may be formed to be stiffer proximate the inside periphery 3341 of the ring strap portion 3340.

The ring strap portion 3340 also comprises an inferior ventilation portion 3350 provided between the pair of lower strap portions 3320. As shown in FIGS. 8 and 9, the inferior ventilation portion 3350 comprises an inferior edge 3351 spaced from an inferior edge 3343 of the ring strap portion 3340. The inferior edge 3351 of the inferior ventilation portion 3350 and the inferior edge 3343 of the ring strap portion 3340 are both arcuate in this example of the technology.

The inferior edge 3351 of the ventilation portion 3350 comprises a greater curvature than the inferior edge 3343 of the ring strap portion 3340. This greater curvature of the inferior edge 3351 of the ventilation portion 3350 provides a maximum spacing between the inferior edge 3351 of the ventilation portion 3350 and the inferior edge 3343 of the ring strap portion 3340 at or proximate the sagittal plane of the patient's head in use. The ventilation portion 3350 and/or the ring strap portion 3340 in the vicinity of the ventilation portion 3350 may be in contact with or in close proximity to a patient's neck. Additionally, the mesh construction of the ventilation portion 3350 may be rougher than the non-meshed surface of the ring strap portion 3340. Accordingly, providing a spacing between the inferior edge 3351 of the ventilation portion 3350 and the inferior edge 3343 may reduce the amount of the meshed fabric in contact with the patient's skin. This may be particularly advantageous when the contact between the ring strap portion 3340 and the patient's skin occurs while the ring strap portion 3340 is under tension and for a prolonged period of time, as occurs during use of the patient interface 3000.

The headgear strap 3301 of the positioning and stabilising structure 3300 shown in FIG. 16 also comprises a ventilation portion 3350. The ventilation portion 3350 in this example is provided in the neck strap portion 3334. The ventilation portion 3350 may take the same form and comprise the same properties as described above in relation to the ventilation portions 3350 of the positioning and stabilising structures 3300 and headgear straps 3301 shown in FIGS. 7-15. In this example, the rigidised portion 3345 surrounds the ventilation portion 3350.

It is noted that the jersey knit structure (e.g., single jersey knit, double jersey knit), the pique knit structure, and the pique mesh knit structure refer to textiles or textile portions formed respectively by jersey, pique, and pique mesh knitting techniques which form different knit structures due to their different manners of interlacing yarns, as those skilled in the art will understand.

5.3.3.4 Blind Guides

As discussed above, some or all of the headgear strap portions of the positioning and stabilising structure 3300 may comprise fastening portions 3360. As shown in FIGS. 7, 8 and 16, the upper strap portions 3310 and lower strap portions 3320 each comprise a fastening portion 3360 proximate the end of the respective strap portion. The fastening portions 3360 are each structured and/or arranged to allow the respective strap portion to be looped back and fastened onto itself.

In examples, the fastening portions 3360 may comprise hook-and-loop material and/or magnets. This allows each of the upper strap portions 3310 and lower strap portions 3320 to be connected to other components of the patient interface 3000, such as the frame 3500 or, in other examples, directly to the plenum chamber 3200. The upper strap portions 3310 and lower strap portions 3320 may connect directly to the frame 3500 through slots or other openings or may connect to headgear clips which then connect to the frame 3500. In one example, as shown in FIGS. 7 and 8, the upper strap portions 3310 each connect to an upper strap connection point 3510 on the frame 3500. Each upper strap connection point 3510 comprises a slot through which the fastening portion 3360 of an upper strap portion 3310 can pass, enabling an end of the upper strap portion 3310 to be secured back onto an intermediate/middle portion of the upper strap portion 3310. In this example, the lower strap portions 3320 connect to headgear clips 3322. Each lower strap portion 3320 passes through a slot formed in a headgear clip 3322 and is then looped back and secured to itself. The headgear clip 3322 is then connected to the frame 3500. In this example, the headgear clips 3322 and frame 3500 each comprise magnets enabling the headgear clips 3322 to be secured to (and also quickly released from) predetermined parts of the frame 3500 under magnetic attraction. In the example shown in FIG. 16, the fastening portions 3360 of the upper headgear strap portions 3310 may loop through eyelets on headgear conduits of a positioning and stabilising structure 3300. The fastening portions 3360 of the lower headgear straps 3320 may loop thought slots on a plenum chamber 3200 of the patient interface 3000 or loop through headgear clips which connect to the plenum chamber 3200, in a similar manner to that shown in FIG. 7.

One or more of the strap portions of the positioning and stabilising structure 3300 may comprise at least one blind guide 3370. In examples of the present technology in which the headgear strap portions comprise a knitted fabric, the blind guides 3370 may also be formed by the knitted fabric. In some examples, a headgear strap is formed by flat knitting and a blind guide is also formed by flat knitting during the same process. The blind guide 3370 may provide a tactile indication of the location of a fastening portion 3360 on a strap. The blind guides 3370 may be features that the patient can feel on the surface of the headgear straps, configured to aid the user in manipulating the headgear straps (e.g. fitting and adjusting the straps), especially when the mask has been donned by the patient and the patient cannot see the headgear straps. The blind guides 3370 may be raised bumps, a raised profile or other tactile features to guide the user in securing the straps back onto themselves after looping the strap through slots or eyelets provided to the mask frame or headgear clips. In other examples of the present technology the blind guides 3370 may comprise recessed portions.

As shown in FIGS. 7, 8 and 16, each of the upper strap portions 3310 and the lower strap portions 3320 comprises a blind guide 3370 in the fastening portion 3360 of the respective strap. Each blind guide 3370 provides a tactile indication of the location of a fastening portion 3360 on a respective one of the upper strap portions 3310 and the lower strap portions 3320. In some examples, blind guides 3370 may be provided to overhead strap portions of the positioning and stabilising structure 3300 as well.

FIG. 11 shows an exploded view of a fastening portion 3360 of a strap of a positioning and stabilising structure 3300. In the illustrated example, the strap is an upper strap portion 3310 of the positioning and stabilising structure 3300 but the features of the fastening portion 3360 and blind guide 3370 may be applied to the lower strap portions 3320 or other straps/strap portions of the positioning and stabilising structures 3300 according to examples of the present technology. The upper strap portion 3310 comprises a non-patient-contacting surface on which the blind guide 3370 is provided. The blind guide 3370 may comprise a raised portion with respect to the non-patient-contacting surface of the upper strap portion 3310. The raised portion may surround at least part of the fastening portion 3360. As illustrated in FIGS. 10 and 11, the raised portion comprises an elongate raised profile on the non-patient-contacting surface of the strap. In this example, the elongate raised profile of the blind guide 3370 is provided at one or more edges of the fastening portion 3360. The elongate raised profile may be provided at edges of the fastening portion 3360 which in use are superior, posterior and inferior edges. The blind guide 3370 may be provided around a periphery of a fastening portion 3360, for example on one, two or more sides thereof.

In other examples of the present technology, a strap of a positioning and stabilising structure 3300 may comprise a recessed profile being recessed with respect to the non-patient-contacting surface. The recessed portion may surround at least part of a fastening portion 3360 on the strap. Any suitable features of shape and location of a raised blind guide described herein may be applied to a recessed blind guide according other examples of the present technology. Likewise, any of the illustrated examples of positioning and stabilising structures according to the present technology may comprise recessed blind guides instead of raised blind guides, in other examples of the technology. For example, a recessed blind guide may be formed by an elongate recessed profile and may surround three more sides of a fastening portion 3360. The recessed profile may be formed by a reduced thickness of the strap. The present technology includes blind guides formed by other features as well, such regions of higher rigidity, portions of a headgear strap having surface finishes/textures that are different from adjacent regions of the strap. The knitting pattern, knitting density and/or yarn material/thickness could be varied in order to provide a user with tactile indication of the location of the fastening portion on the strap.

In some examples of the present technology, the elongate raised profile of the blind guide 3370 is rounded. This may make the blind guide 3370 more comfortable for the patient to touch, more aesthetically pleasing and may make the positioning and stabilising structure 3300 more durable due to a smoother transition between the raised portion and the non-patient-contacting surface on which it is provided.

The raised portion of the blind guide 3370 may be formed by increased thickness of the strap in comparison to adjacent regions of the strap. The extra material forming the increased thickness may be provided to the non-patient-contacting surface.

The fastening portions 3360 of the straps may comprise a hook-and-loop fastening material (e.g. Velcro™). The fastening portion 3360 may comprise an end portion 3361 comprising one of a hook material and a loop material provided to the non-patient-contacting surface and an intermediate portion 3363 comprising the other of the hook material and the loop material provided to the non-patient-contacting surface. The intermediate portion 3363 may be provided adjacent the end portion 3361 of the strap. In the example shown in FIG. 11, the fastening portion 3360 comprises a hook portion 3362 and a loop portion 3364. The hook portion 3362 is provided to the end portion 3361 of the upper strap portion 3310. The loop portion 3364 is provided to the intermediate portion 3363 of the upper strap portion 3310. In other examples, the hook portion 3362 may be provided to the intermediate portion 3363 of the strap, and the loop portion 3364 may be provided to the end portion 3361 of the strap. The hook portion 3362 is able to releasably attached to the loop portion 3364. This means that, once the upper strap portion 3310 is threaded through an opening in another component (e.g. a slot formed in the frame 3500), the end portion 3361 can be looped back towards the intermediate portion 3363 and the hook portion 3362 can be releasably attached to the loop portion 3364. The blind guide 3370 may surround only one of the end portion 3361 and intermediate portion 3363. In the example shown in FIG. 11, the blind guide 3370 is provided around only the intermediate portion and 3363 and loop portion 3364. As illustrated, the blind guide 3370 is provided around three sides of the loop portion 3364.

The intermediate portion 3363 may be longer than the end portion 3361. This may enable the end portion 3361 to be fastened to a range of locations along the intermediate portion 3363, increasing the amount of length adjustability of the strap. In some examples, the intermediate portion 3363 is several times longer than the end portion 3361.

The strap portion comprising the blind guide 3370 (e.g. the upper strap portions 3310, the lower strap portion 3320 or any other strap portion in other examples of the technology) and the blind guide 3370 itself may be formed together during a single knitting process. The blind guide 3370 may comprise a pique knitting structure. The strap may comprise a single jersey knitting structure. In alternative examples of the technology, the strap may comprise a double jersey loop formation. A strap and a blind guide 3370 may be integrally formed.

The hook portions 3362 and the loop portions 3364 may be formed separately and then assembled with the respective strap portions. They may be adhered to or sewn into the strap portions of the positioning and stabilising structure 3300. Alternatively, one or both of the hook portion 3362 and loop portion 3364 may be ultrasonically welded to the headgear strap. In other examples of the technology, one or both of the hook portion 3362 and loop portion 3364 are knitted. The hook portion 3362 and/or the loop portion 3364 may be formed during the same knitting process used to form the strap portion to which they are provided. The knitting process may comprise flat knitting. The hook portions 3362 and loop portions 3364 may be formed from nylon. This may reduce skin irritation through superior breathability, and may provide a soft loop that avoids abrasiveness against the patient's skin. The hook portion 3362 and loop portion 3364 may be die cut.

The upper strap portion 3310 and/or other strap portions may comprise a visual guide 3366 indicating the end portion of the strap, as shown in FIG. 11. The visual guide 3366 may surround the hook portion 3362. The visual guide 3366 may not be raised above the surface of the strap portion and may be a visual guide in the form of coloured fabric. The visual guide 3366 may also, or alternatively, facilitate assembly of the hook portions 3362 to the strap portions to which they are to be fixed during manufacturing.

As illustrated in FIGS. 8 and 16, each of the upper strap portions 3310 and lower strap portion 3320 comprises a fastening portion 3360. Each of the fastening portions 3360 comprises a hook portion 3362 provided to an end portion 3361 of the respective strap portion and a loop portion 3364 provided to an intermediate portion 3363 of the respective strap portion. In other examples of the technology, only the upper strap portions 3310, only the lower strap portions 3320, or neither of the strap portions, have this configuration. In some examples, the knitting process used to form the headgear strap portions is configured to precisely provide a predetermined level of stiffness to the strap portions such that adjustability and the blind guides are not required. In some examples, this predetermined level of stiffness may be determined based on the specific shape and size of the patient's head as determined by a scan.

In some examples, the positioning and stabilising structure 3300 may not have lower strap portions 3320 and may only have upper strap portions 3310. Such an arrangement may be suited for a patient interface 3000 of an "under the nose" type (e.g. having a seal-forming structure 3100 in the form of nasal pillows or nasal cradle). In such an example, the upper strap portions 3310 may have the fastening portions 3360 and blind guides 3370 described above. A positioning and stabilising structure 3300 that has upper strap portions 3310 but not lower strap portions 3320 may have a ring strap portion 3340 having a superior portion 3302 and an inferior portion 3304. One or both of the superior portion 3302 and the inferior portion 3304 may be adjustable by the patient. In such an example, the superior portion 3302 and/or the inferior portion 3304 may be split into two strap portions connected by a buckle (or a similar component having to opening through which straps can be fed). Each of the two strap portions forming the superior portion 3302 and/or inferior portion 3304 may comprise features of the fastening portion 3360 and/or blind guides 3370 as described above with reference to FIG. 11.

The blind guides 3370 may be stretchable in some examples of the technology and non-stretchable in other examples. A strap portion to which the blind guide 3370 is provided may be stretchable as a whole in order to provide some extensibility under tension although in some examples only a select region of the strap portion may extend in length. If the region of a strap portion to which a blind guide 3370 is provided is stretchable, the blind guide 3370 may also be formed to be stretchable (e.g. by using a knitting process that enables the blind guide to elastically extend with the strap on which it is formed). In some examples, a blind guide 3370 may be provided to a part of strap that is not stretchable (for example if the strap has a stretchable portion elsewhere along its length). In such an example, the blind guide 3370 may not be stretchable.

As shown in FIG. 12, an end portion blind guide 3371 may be provided to the patient-contacting side of the headgear strap 3301 to provide a tactile indication of the end portion 3361 of the strap portion. In use, once the strap portion has been fed through a slot in the frame 3500, the surface on which the blind guide 3371 is formed will be looped over the patient-contacting side of the headgear strap 3301.

5.3.4 Vent

In one form, the patient interface 3000 includes a vent structure 3400 constructed and arranged to allow for the washout of exhaled gases, e.g. carbon dioxide.

In certain forms the vent structure 3400 is configured to allow a continuous vent flow from an interior of the plenum chamber 3200 to ambient whilst the pressure within the plenum chamber is positive with respect to ambient. The vent structure 3400 is configured such that the vent flow rate has a magnitude sufficient to reduce rebreathing of exhaled $CO_2$ by the patient while maintaining the therapeutic pressure in the plenum chamber in use.

One form of vent structure 3400 in accordance with the present technology comprises a plurality of holes, for example, about 20 to about 80 holes, or about 40 to about 60 holes, or about 45 to about 55 holes.

The vent structure 3400 may be located in the plenum chamber 3200. Alternatively, the vent structure 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT DEVICE

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 HUMIDIFIER 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components 5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 BREATHING WAVEFORMS

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 GLOSSARY

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Anatomy 5.8.2.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.2.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.2.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.3 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.4.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.4.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.4.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

| | |
|---|---|
| Patient | 1000 |
| Bed partner | 1100 |
| Patient interface | 3000 |
| Seal-forming structure | 3100 |
| Plenum chamber | 3200 |
| Chord | 3210 |
| Superior point | 3220 |
| Inferior point | 3230 |
| Positioning and stabilising structure | 3300 |
| Headgear strap | 3301 |
| Superior portion of the ring strap portion | 3302 |
| Inferior portion of the ring strap portion | 3304 |
| Upper strap portions | 3310 |
| Lower strap portions | 3320 |
| Headgear clip | 3322 |
| Overhead strap portion | 3330 |
| Lateral connecting strap portion | 3332 |
| Neck strap portion | 3334 |
| Ring strap portion | 3340 |
| Inside periphery of the ring strap portion | 3341 |
| Outside periphery of the ring strap portion | 3342 |
| Inferior edge of the ring strap portion | 3343 |
| Rigidised portion | 3345 |
| Superior stretchable portion | 3346 |
| Inferior stretchable portion | 3347 |
| Ventilation portion | 3350 |
| Inferior edge of the ventilation portion | 3351 |
| Fastening portion | 3360 |
| End portion | 3361 |
| Hook portion | 3362 |
| Intermediate portion | 3363 |
| Loop portion | 3364 |
| Blind guide | 3370 |
| End portion blind guide | 3371 |
| Vent structure | 3400 |
| Frame | 3500 |
| Upper strap connection point | 3510 |
| Cushion assembly | 3580 |
| Cushion assembly | 3590 |
| Connection port | 3600 |
| Forehead support | 3700 |
| Headgear conduits | 3900 |
| Lateral portion | 3901 |
| Junction | 3903 |
| RPT device | 4000 |
| External housing | 4010 |
| Upper portion | 4012 |
| Lower portion | 4014 |
| Panel | 4015 |
| Chassis | 4016 |
| Handle | 4018 |
| Pneumatic block | 4020 |
| Air filter | 4110 |
| Inlet air filter | 4112 |
| Outlet air filter | 4114 |
| Muffler | 4120 |
| Inlet muffler | 4122 |
| Outlet muffler | 4124 |
| Pressure generator | 4140 |
| Blower | 4142 |
| Motor | 4144 |
| Anti-spill back valve | 4160 |
| Air circuit | 4170 |
| Supplemental oxygen | 4180 |
| Electrical components | 4200 |
| Printed circuit board assembly (PCBA) | 4202 |
| Electrical power supply | 4210 |
| Input devices | 4220 |
| Transducers | 4270 |
| Humidifier | 5000 |
| Humidifier inlet | 5002 |
| Humidifier outlet | 5004 |
| Humidifier base | 5006 |
| Humidifier reservoir | 5110 |
| Conductive portion | 5120 |
| Humidifier reservoir dock | 5130 |
| Locking lever | 5135 |
| Water level indicator | 5150 |
| Heating element | 5240 |

The invention claimed is:

1. A patient interface for sealed delivery of a flow of air at a continuously positive pressure with respect to ambient air pressure to an entrance to a patient's airways including at least an entrance of a patient's nares, wherein the patient interface is configured to maintain a therapy pressure in a range of about 4 cmH2O to about 30 cmH2O above ambient air pressure in use, throughout a patient's respiratory cycle, while the patient is sleeping, to ameliorate sleep disordered breathing; said patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient, a seal-forming structure constructed and arranged to form a seal with a region of a patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient air, said vent structure being sized and shaped to maintain the therapeutic pressure in the plenum chamber in use;

wherein the patient interface is configured to allow the patient to breathe from the ambient air through the patient's mouth in the absence of the flow of air through the plenum chamber inlet port, or the patient interface is configured to leave the patient's mouth uncovered;

wherein the positioning and stabilising structure comprises:

a knitted ring strap portion having a superior portion configured to overlay the parietal bones of the patient's head in use and having an inferior portion configured to overlay or lie inferior to the occipital bone of the patient's head in use, the ring strap portion defining a loop and having an inside periphery and an outside periphery; and a pair of upper strap portions, each configured to connect between the ring strap portion and a cushion assembly in use on a respective side of the patient's head superior to the otobasion superior;

wherein the ring strap portion comprises a first knit structure forming a first portion extending along at least a portion of the outside periphery of the ring strap portion, wherein the ring strap portion comprises a second rigidised knit structure forming a second rigidised portion provided proximate the inside periphery of the ring strap portion, and wherein the first knit structure is a different knit structure than the second rigidised knit structure, and the first portion has increased stretchability as compared to the second rigidised portion.

2. The patient interface of claim 1, wherein the second rigidised portion is provided substantially along the entire length of the loop defined by the ring strap portion.

3. The patient interface of claim 1, wherein the first portion extends along the entire outside periphery of the ring strap portion.

4. The patient interface of claim 3, wherein the second rigidised portion defines at least a portion of the inside periphery of the ring strap portion.

5. The patient interface of claim 3, wherein the second rigidised portion forms substantially the entire inside periphery of the ring strap portion.

6. The patient interface of claim 1, wherein the first portion is directly adjacent the second rigidised portion.

7. The patient interface of claim 1, wherein the upper strap portions are stretchable.

8. The patient interface of claim 1, wherein the second rigidised portion is substantially non-stretchable.

9. The patient interface of claim 1, wherein the ring strap portion comprises rounded edges.

10. The patient interface of claim 1, wherein the second rigidised portion comprises an increased material thickness relative to regions of the ring strap portion other than the second rigidised portion.

11. The patient interface of claim 10, wherein a patient-contacting side of the ring strap portion is substantially flat and the increased material thickness is provided to a non-patient-contacting side of the ring strap portion.

12. The patient interface of claim 10, wherein the ring strap portion comprises a thickness of 4 mm in the second rigidised portion.

13. The patient interface of claim 10, wherein the ring strap portion comprises a thickness of 2.5 mm in regions of the ring strap portion other than the second rigidised portion.

14. The patient interface of claim 1, wherein the second rigidised portion is larger in regions of the ring strap portion relatively proximate the upper strap portions than in regions of the ring strap portion relatively distal to the upper strap portions.

15. The patient interface of claim 14, wherein the second rigidised portion is wider in the regions of the ring strap portion relatively proximate the upper strap portions than in the other regions of the ring strap portion relatively distal to the upper strap portions.

16. The patient interface of claim 1, wherein the ring strap portion comprises at least one ventilation portion structured and/or arranged to provide increased breathability through the ring strap portion at the ventilation portion.

17. The patient interface of claim 16, wherein the ventilation portion comprises a knitted fabric having a pique mesh knitting structure.

18. The patient interface of claim 16, wherein stretchability in the ventilation portion is less than stretchability in regions of the ring strap portion other than the ventilation portions.

19. The patient interface of claim 16, wherein the second rigidised portion surrounds the ventilation portion.

20. The patient interface of claim 16, wherein the ring strap portion comprises a pair of superior ventilation portions, each provided proximate a respective upper strap portion of the pair of upper strap portions.

21. The patient interface of claim 20, wherein the second rigidised portion surrounds each of the superior ventilation portions.

22. The patient interface of claim 21, wherein the second rigidised portion comprises a higher material thickness on a posterior side of each of the superior ventilation portions than on an anterior side of each of the superior ventilation portions.

23. The patient interface of claim 1, wherein the positioning and stabilising structure comprises a pair of lower strap portions, each lower strap portion configured to connect between the ring strap portion and the cushion assembly in use on a respective side of the patient's head inferior to the otobasion superior.

24. The patient interface of claim 23, wherein the ring strap portion comprises an inferior ventilation portion provided between the pair of lower strap portions.

25. The patient interface of claim 24, wherein the inferior ventilation portion comprises an inferior edge spaced from an inferior edge of the ring strap portion.

26. The patient interface of claim 25, wherein the inferior edge of the inferior ventilation portion comprises a greater curvature than the inferior edge of the ring strap portion to create a maximum spacing between the inferior edge of the inferior ventilation portion and the inferior edge of the ring strap portion at or proximate a sagittal plane of the patient's head in use.

27. The patient interface of claim 23, wherein the lower strap portions are stretchable.

28. The patient interface of claim 1, wherein the entire ring strap portion comprises a knitted fabric structure.

29. The patient interface of claim 28, wherein the ring strap portion is formed by flat knitting.

30. The patient interface of claim 28, wherein the ring strap portion comprises a single jersey knitting structure.

31. The patient interface of claim 28, wherein the ring strap portion comprises a double jersey loop formation knitting structure.

32. The patient interface of claim 28, wherein the second rigidised portion comprises a pique knitting structure.

33. The patient interface of claim 1, wherein the superior portion of the ring strap portion comprises a pair of overhead strap portions adjustably connected to each other proximate a sagittal plane of the patient's head.

34. The patient interface of claim 33, wherein the overhead strap portions are adjustably connected with a buckle.

35. The patient interface of claim 33, wherein the overhead strap portions comprise hook and loop fastening material to allow each of the overhead strap portions to be passed through a portion of the buckle and secured back onto itself.

36. The patient interface of claim 1, wherein the positioning and stabilising structure comprises a frame coupled to the plenum chamber, the upper strap portions being configured to connect to the frame.

* * * * *

UNITED STATES PATENT AND TRADEMARK OFFICE
CERTIFICATE OF CORRECTION

PATENT NO. : 12,357,784 B2
APPLICATION NO. : 17/431543
DATED : July 15, 2025
INVENTOR(S) : Wai Hoong Leng It is certified that error appears in the above-identified patent and that said Letters Patent is hereby corrected as shown below:

In the Claims

Claim 15, Column 57, Line 50:
"the other regions of the ring strap portion relatively distal to"
Should read:
"the regions of the ring strap portion relatively distal to".

Claim 18, Column 57, Lines 61-62:
"regions of the ring strap portion other than the ventilation portions."
Should read:
"regions of the ring strap portion other than the ventilation portion.".

Signed and Sealed this
Thirteenth Day of January, 2026

John A. Squires
*Director of the United States Patent and Trademark Office*